(12) United States Patent
DeVries et al.

(10) Patent No.: US 7,849,854 B2
(45) Date of Patent: *Dec. 14, 2010

(54) PORTABLE DRAG COMPRESSOR POWERED MECHANICAL VENTILATOR

(75) Inventors: Douglas F. DeVries, Yucaipa, CA (US); Michael J. Cegielski, Norco, CA (US); Warner V. Graves, Jr., Hemet, CA (US); Malcolm R. Williams, San Clemente, CA (US); Michael B. Holmes, Riverside, CA (US)

(73) Assignee: Bird Products Corporation, Palm Springs, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/935,577

(22) Filed: Sep. 7, 2004

(65) Prior Publication Data

US 2005/0150494 A1 Jul. 14, 2005

Related U.S. Application Data

(60) Division of application No. 10/458,211, filed on Jun. 10, 2003, now Pat. No. 6,877,511, which is a continuation of application No. 09/050,555, filed on Mar. 30, 1998, now abandoned, which is a continuation of application No. 08/794,296, filed on Feb. 3, 1997, now Pat. No. 5,868,133, which is a continuation of application No. 08/324,172, filed on Oct. 14, 1994, now abandoned, application No. 10/935,577, which is a continuation of application No. 10/458,211, filed on Jun. 10, 2003, now Pat. No. 6,877,511.

(30) Foreign Application Priority Data

Jul. 31, 2001 (NO) .................................. 20013747

(51) Int. Cl.
*A62B 7/00* (2006.01)
*A62B 9/00* (2006.01)
*A62B 9/02* (2006.01)

(52) U.S. Cl. ............................ 128/205.11; 128/200.24; 128/204.18; 128/204.21; 128/205.24

(58) Field of Classification Search ............ 128/204.18, 128/204.21, 205.11, 205.18, 200.24, 203.12, 128/205.24; 137/599.05
See application file for complete search history.

(56) References Cited

U.S. PATENT DOCUMENTS 1,619,286 A 3/1927 Burks (Continued)

FOREIGN PATENT DOCUMENTS

CA 686705 5/1964

(Continued)

OTHER PUBLICATIONS

Kacmarek, "The Practical Application of Home Mechanical Ventilatory Equipment," J. Neuro Rehab, vol. 6, No. 2, pp. 103-112 (1992).

(Continued)

*Primary Examiner*—Steven O Douglas
*Assistant Examiner*—Annette F Dixon
(74) *Attorney, Agent, or Firm*—Arent Fox LLP

(57) ABSTRACT

A ventilator device and system comprising a rotating compressor, preferably a drag compressor, which, at the beginning of each inspiratory ventilation phase, is accelerated to a sufficient speed to deliver the desired inspiratory gas flow, and is subsequently stopped or decelerated to a basal flow level to permit the expiratory ventilation phase to occur. The ventilator device is small and light weight enough to be utilized in portable applications. The ventilator device is power efficient enough to operate for extended periods of time on internal or external batteries. Also provided is an oxygen blending apparatus which utilizes solenoid valves having specific orifice sizes for blending desired amounts of oxygen into the inspiratory gas flow. Also provided is an exhalation valve having an exhalation flow transducer which incorporates a radio frequency data base to provide an attendant controller with specific calibration information for the exhalation flow transducer.

9 Claims, 8 Drawing Sheets

U.S. PATENT DOCUMENTS

| | | | |
|---|---|---|---|
| 1,793,226 A | 2/1931 | Eggleston | |
| 2,283,844 A | 5/1942 | Brady, Jr. | |
| 2,503,563 A | 4/1950 | Ray | |
| 2,536,691 A | 1/1951 | Miller | |
| 2,586,677 A | 2/1952 | Marrett | |
| 2,770,231 A | 11/1956 | Falk | |
| 2,770,232 A | 11/1956 | Falk | |
| 2,807,217 A | 9/1957 | Krzyszczuk | |
| 2,880,719 A | 4/1959 | Andreasen | |
| 2,892,348 A | 6/1959 | Ekstrom, Jr. | |
| 2,904,035 A | 9/1959 | Andreasen | |
| 2,999,482 A * | 9/1961 | Bower | 91/31 |
| 3,007,490 A | 11/1961 | Passmore | |
| 3,015,963 A | 1/1962 | Terry | |
| 3,043,302 A | 7/1962 | Spears | |
| 3,095,820 A | 7/1963 | Sanborn et al. | |
| 3,306,570 A | 2/1967 | Cooksley | |
| 3,324,799 A | 6/1967 | Terrano | |
| 3,351,057 A | 11/1967 | Goodyear | |
| 3,355,095 A | 11/1967 | Hollenberg | |
| 3,356,033 A | 12/1967 | Ullery | |
| 3,356,034 A | 12/1967 | Knowles | |
| 3,360,193 A | 12/1967 | Harris | |
| 3,374,410 A | 3/1968 | Cronquist | |
| 3,392,675 A | 7/1968 | Taylor | |
| 3,395,853 A | 8/1968 | Zoehfeld | |
| 3,403,556 A | 10/1968 | Koester | |
| 3,416,054 A | 12/1968 | Galles | |
| 3,450,382 A | 6/1969 | Calim | |
| 3,488,030 A | 1/1970 | Hulme | |
| 3,545,890 A | 12/1970 | Hubbard | |
| 3,569,813 A | 3/1971 | Clark | |
| 3,579,279 A | 5/1971 | Inaba | |
| 3,586,953 A | 6/1971 | Markkamen | |
| 3,593,735 A * | 7/1971 | Reiher | 137/88 |
| 3,675,633 A | 7/1972 | Nakajima | |
| 3,759,099 A | 9/1973 | McGregor | |
| 3,795,145 A | 3/1974 | Miller | |
| 3,813,592 A | 5/1974 | Ryberg | |
| 3,820,539 A | 6/1974 | Ollivier | |
| 3,839,662 A | 10/1974 | N'Gayen Van | |
| 3,840,006 A | 10/1974 | Buck et al. | |
| 3,842,828 A | 10/1974 | Bird | |
| 3,848,617 A * | 11/1974 | Dray | 137/88 |
| 3,849,024 A | 11/1974 | Masai | |
| 3,896,837 A | 7/1975 | Rohling | |
| 3,904,174 A | 9/1975 | Glese | |
| 3,906,792 A | 9/1975 | Miller | |
| 3,910,112 A | 10/1975 | Gerlach | |
| 3,951,567 A | 4/1976 | Rohs | |
| 3,961,627 A | 6/1976 | Ernst | |
| 3,964,310 A | 6/1976 | Stenberg | |
| 3,968,416 A | 7/1976 | Leenhouts | |
| 3,985,131 A | 10/1976 | Buck | |
| 4,006,634 A | 2/1977 | Billette | |
| 4,024,447 A | 5/1977 | Epstein | |
| 4,027,636 A | 6/1977 | Yamamoto | |
| 4,031,448 A | 6/1977 | Adachi | |
| 4,036,221 A * | 7/1977 | Hillsman et al. | 128/204.23 |
| RE29,383 E * | 9/1977 | Gallatin et al. | 137/14 |
| 4,081,736 A | 3/1978 | Leenhouts | |
| 4,083,245 A | 4/1978 | Osborn | |
| 4,087,732 A | 5/1978 | Pritchard | |
| 4,094,285 A | 6/1978 | Oyama | |
| 4,098,271 A * | 7/1978 | Maddock | 128/202.22 |
| 4,107,594 A | 8/1978 | Jacobs | |
| RE29,778 E | 9/1978 | Stewart | |
| 4,112,757 A | 9/1978 | Hayward | |
| 4,114,601 A | 9/1978 | Abels | |
| 4,119,902 A | 10/1978 | Newell | |
| 4,121,578 A | 10/1978 | Torzala | |
| 4,126,818 A | 11/1978 | Taylor | |
| 4,126,821 A | 11/1978 | Cannon | |
| 4,148,311 A * | 4/1979 | London et al. | 128/204.26 |
| 4,153,021 A | 5/1979 | Hattori | |
| 4,158,351 A | 6/1979 | Ando | |
| 4,171,697 A | 10/1979 | Arion | |
| 4,176,687 A | 12/1979 | Ensign | |
| 4,177,830 A | 12/1979 | Munson | |
| 4,181,108 A | 1/1980 | Bellicardi | |
| 4,186,737 A * | 2/1980 | Valenta et al. | 128/203.28 |
| 4,191,215 A * | 3/1980 | Gonner | 137/870 |
| 4,193,301 A | 3/1980 | Ferrentino | |
| 4,199,132 A | 4/1980 | deMey, II | |
| 4,204,536 A | 5/1980 | Albarda | |
| 4,215,681 A * | 8/1980 | Zalkin et al. | 128/204.21 |
| 4,232,666 A * | 11/1980 | Savelli et al. | 128/203.25 |
| 4,235,105 A | 11/1980 | Walters | |
| 4,236,546 A * | 12/1980 | Manley et al. | 137/88 |
| 4,256,100 A * | 3/1981 | Levy et al. | 128/204.21 |
| 4,256,101 A | 3/1981 | Ellestad | |
| 4,266,573 A | 5/1981 | Braatz | |
| 4,267,827 A * | 5/1981 | Rauscher et al. | 600/3 |
| 4,281,651 A | 8/1981 | Cox | |
| 4,285,496 A | 8/1981 | Coles | |
| 4,304,136 A | 12/1981 | McCabe | |
| 4,323,064 A | 4/1982 | Hoenig | |
| 4,325,672 A | 4/1982 | Sixsmith | |
| 4,326,513 A | 4/1982 | Schulz | |
| 4,333,453 A | 6/1982 | Rodder | |
| 4,336,590 A | 6/1982 | Jacq | |
| 4,350,050 A | 9/1982 | Nelson | |
| 4,368,646 A | 1/1983 | Rogg | |
| 4,393,869 A | 7/1983 | Boyarsky | |
| 4,401,116 A | 8/1983 | Fry | |
| 4,421,113 A | 12/1983 | Gedeon | |
| 4,448,192 A | 5/1984 | Stawitcke | |
| 4,457,304 A | 7/1984 | Molnar | |
| 4,457,339 A | 7/1984 | Juan | |
| 4,459,982 A * | 7/1984 | Fry | 128/204.23 |
| 4,474,068 A | 10/1984 | Knetsch | |
| 4,484,554 A | 11/1984 | Nakajima | |
| 4,493,614 A | 1/1985 | Chu | |
| 4,524,804 A | 6/1985 | Goedecke | |
| 4,527,557 A * | 7/1985 | DeVries et al. | 128/204.23 |
| 4,535,816 A | 8/1985 | Feder | |
| 4,540,018 A | 9/1985 | Dantlgraber | |
| 4,548,382 A | 10/1985 | Otting | |
| 4,552,027 A | 11/1985 | Larner | |
| 4,561,408 A | 12/1985 | Jenkins | |
| 4,570,631 A | 2/1986 | Durkan | |
| 4,576,159 A | 3/1986 | Hahn | |
| 4,579,145 A | 4/1986 | Leiber | |
| 4,587,967 A | 5/1986 | Chu | |
| 4,602,653 A | 7/1986 | Ruiz-Vela | |
| 4,604,902 A | 8/1986 | Sabin | |
| 4,606,340 A | 8/1986 | Ansite | |
| 4,611,591 A | 9/1986 | Inui | |
| 4,614,122 A | 9/1986 | Graves | |
| 4,617,637 A | 10/1986 | Chu | |
| 4,619,139 A | 10/1986 | Rosaen | |
| 4,627,860 A * | 12/1986 | Rowland | 96/111 |
| 4,635,631 A | 1/1987 | Izumi | |
| 4,677,603 A | 6/1987 | Kenjyo | |
| 4,688,433 A | 8/1987 | Silverwater | |
| 4,699,137 A | 10/1987 | Schroeder | |
| 4,702,240 A | 10/1987 | Chaoui | |
| 4,757,943 A * | 7/1988 | Sperling et al. | 236/12.12 |
| 4,790,194 A | 12/1988 | Bellows | |
| 4,821,709 A * | 4/1989 | Jensen | 128/205.11 |
| 4,821,767 A | 4/1989 | Jackson | |
| 4,838,257 A | 6/1989 | Hatch | |
| 4,840,457 A | 6/1989 | Remer | |
| 4,860,803 A * | 8/1989 | Wells | 141/9 |

| | | | | |
|---|---|---|---|---|
| 4,905,685 A * | 3/1990 | Olsson et al. ......... 128/203.12 |
| 4,957,107 A * | 9/1990 | Sipin .................. 128/204.21 |
| 4,971,052 A | 11/1990 | Edwards |
| 4,993,269 A | 2/1991 | Guillaume |
| 5,044,362 A | 9/1991 | Younes |
| 5,072,729 A | 12/1991 | De Vries |
| 5,099,635 A | 3/1992 | Butkovich |
| 5,107,830 A | 4/1992 | Younes |
| 5,127,400 A | 7/1992 | De Vries |
| 5,148,802 A | 9/1992 | Sanders |
| 5,159,924 A * | 11/1992 | Cegielski et al. ....... 128/203.12 |
| 5,197,895 A | 3/1993 | Stupecky |
| 5,237,987 A * | 8/1993 | Anderson et al. ...... 128/204.18 |
| 5,239,995 A | 8/1993 | Estes |
| 5,245,995 A | 9/1993 | Sullivan et al. |
| 5,263,476 A * | 11/1993 | Henson ............... 128/204.18 |
| 5,299,568 A * | 4/1994 | Forare et al. .......... 128/205.11 |
| 5,299,908 A | 4/1994 | Robbie |
| 5,315,990 A * | 5/1994 | Mondry ............... 128/205.11 |
| 5,329,955 A * | 7/1994 | Gensler et al. ............ 137/7 |
| 5,339,807 A | 8/1994 | Carter |
| 5,374,160 A | 12/1994 | Hablanian |
| 5,390,666 A * | 2/1995 | Kimm et al. .......... 128/204.26 |
| 5,395,210 A | 3/1995 | Yamazaki |
| 5,450,088 A | 9/1995 | Meier et al. |
| 5,499,900 A | 3/1996 | Khmara |
| 5,520,333 A * | 5/1996 | Tofte ..................... 239/10 |
| 5,558,086 A * | 9/1996 | Smith et al. ........... 128/204.26 |
| 5,577,496 A | 11/1996 | Blackwood et al. |
| 5,593,478 A * | 1/1997 | Hill et al. .................. 96/11.1 |
| 5,628,615 A | 5/1997 | Asabuki |
| 5,664,563 A * | 9/1997 | Schroeder et al. ...... 128/204.25 |
| 5,697,228 A * | 12/1997 | Paige ..................... 62/615 |
| 5,868,133 A * | 2/1999 | DeVries et al. ........ 128/204.21 |
| 5,893,275 A * | 4/1999 | Henry .................... 62/615 |
| 5,915,834 A * | 6/1999 | McCulloh ............... 366/151.1 |
| 6,283,119 B1 | 9/2001 | Bourdon |
| 6,526,970 B2 * | 3/2003 | DeVries et al. ........ 128/204.21 |
| 6,681,764 B1 * | 1/2004 | Honkonen et al. ..... 128/201.21 |
| 6,877,511 B2 * | 4/2005 | DeVries et al. ........ 128/204.26 |

FOREIGN PATENT DOCUMENTS

| | | |
|---|---|---|
| DE | 2558935 | 7/1977 |
| EP | 0552916 A1 | 7/1993 |
| EP | 0563713 A2 | 10/1993 |
| FR | 2663547 A1 | 12/1981 |
| FR | 2573658 A1 | 5/1986 |
| FR | 2695320 A1 | 3/1994 |
| FR | 2554351 A1 | 5/1995 |
| GB | 2126666 | 3/1984 |
| GB | 216636OA | 5/1986 |
| GB | 2240392 A | 7/1991 |
| JP | 3-105095 | 5/1991 |
| WO | PCT/US82/00795 | 6/1982 |
| WO | WO 91/06832 * | 5/1991 |
| WO | PCT/FR93/00547 | 12/1993 |

OTHER PUBLICATIONS

Tobin, "Principle and Practices of Mechanical Ventilation," New York: McGraw-Hill, Chapters 3, 4, 19, including pp. 65-67, 111-115, 118-120, 127-138 and 427-453 (Apr. 22, 1994) ("Airox Reference").

International Search Report of International Application No. PCT/US95/08499 (WO 96/11717), dated Nov. 28, 1995.

Supplementary Partial European Search Report of Application No. 95 92 6628 (EP 0 800 412), dated Jul. 20, 1998.

European Search Report of Application No. 02 00 1850 (EP 1 205 203), dated May 30, 2002.

European Search Report of Application No. 02 00 1849 (EP 1 205 206), dated Jun. 5, 2002.

Partial European Search Report of Application No. 04 07 7065 (EP 1 491 227), dated Nov. 26, 2004.

"Marks Standard Handbook for Mechanical Engineers", 8th Edition, Measurement of Fluid Flow Rate, pp. 16-18.

Westlake Plastics Co.; Thermalux Polysulfone, 1 pg.

"Sandvik 11R51 Stainless Thin Strip"; Thin Strip With a Smooth Finish, Good Shape and High Fatigue Strength, 4 pgs.

Step Motors and Control Systems: Microprocessor Control of STP Motors; S.H. Pollack, Chapter 15: pp. 391-402: 1979.

"Electric Motors & Control Techniques"; Stepper Motor Controllers; Irving M. Gottleib; pp. 183-198; 1982.

"Step Motors & Control Systems"; Drive Circuitry for Step Motors; Benjamin C. Kuo; Chapter 4; pp. 114-143; 1979.

Stepping Motors & Their Microprocessor Controls: Drive System and Circuitry for Open-Loop Control of Stepping Motors: Takashi Kenjo: Chapter 5; pp. 121-165: 1984.

"Servo Ventilator 900B—Service Manual"; Seimens-Elema; 55 pgs; 1979.

Computer printouts containing abstracts of 62 pages.

* cited by examiner

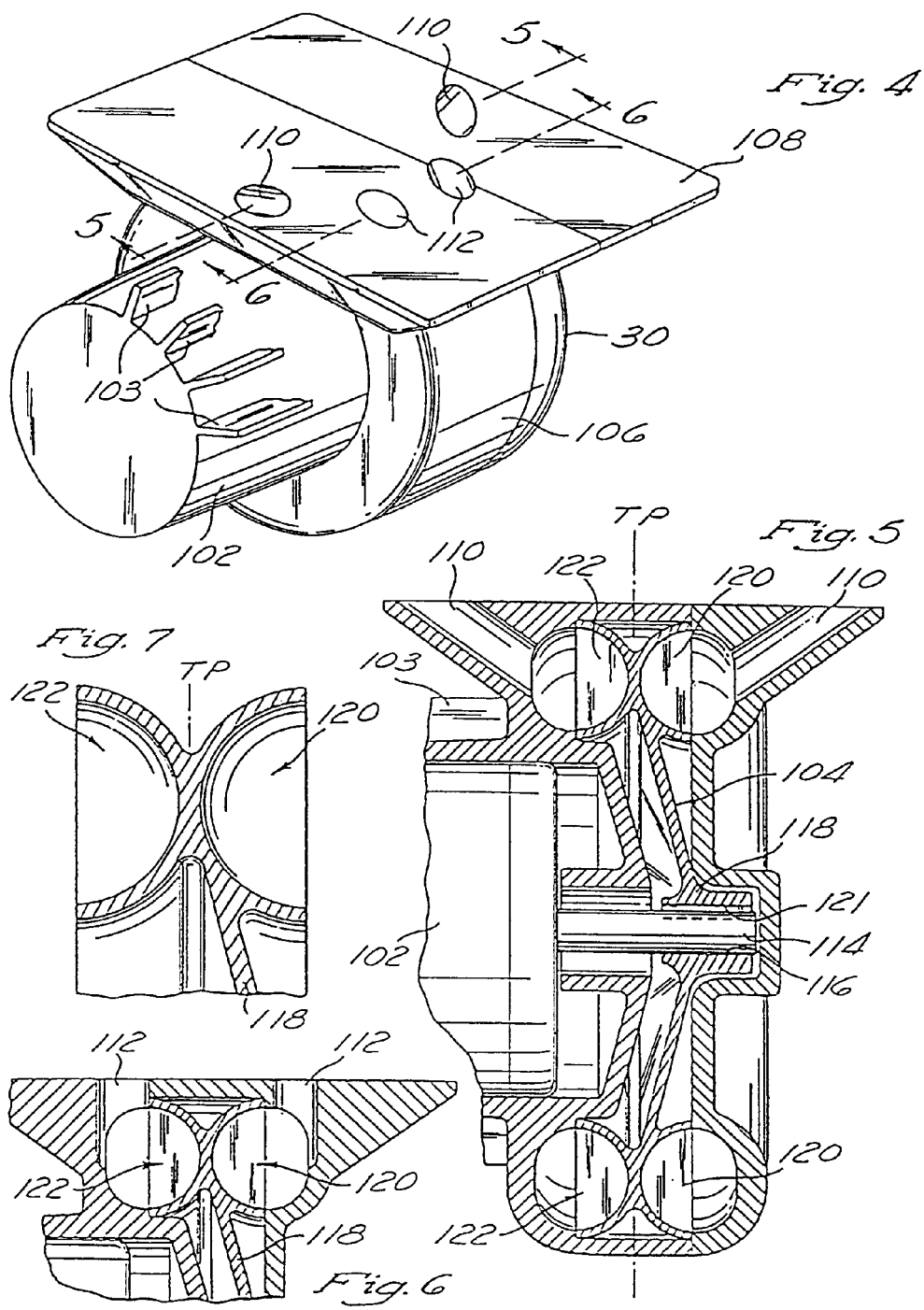

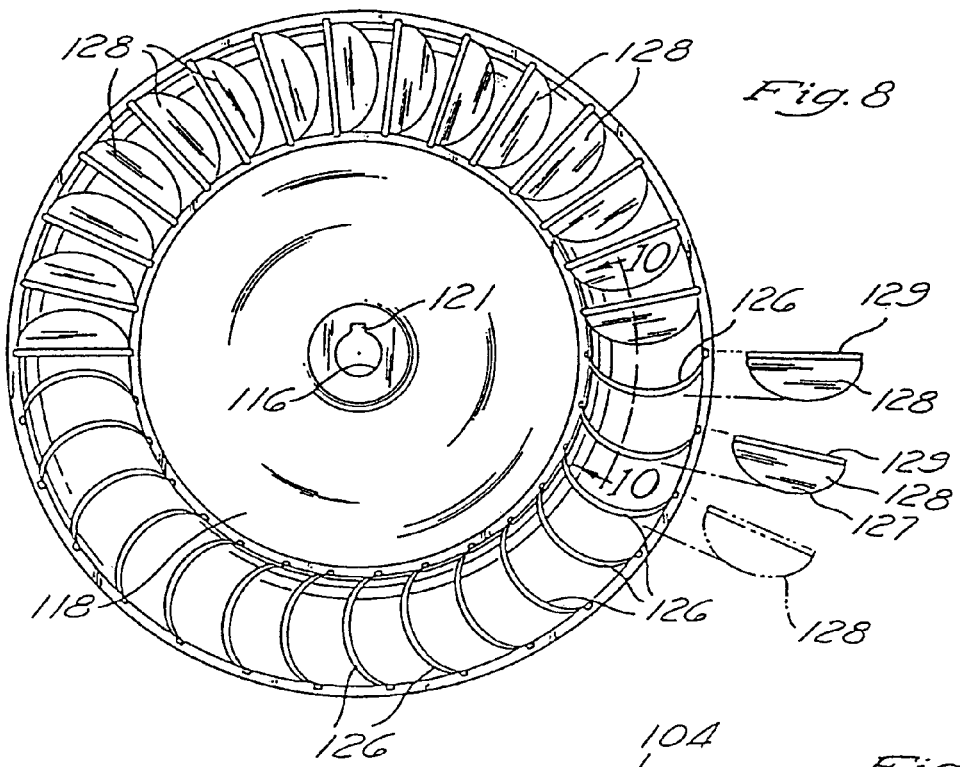
Fig. 8
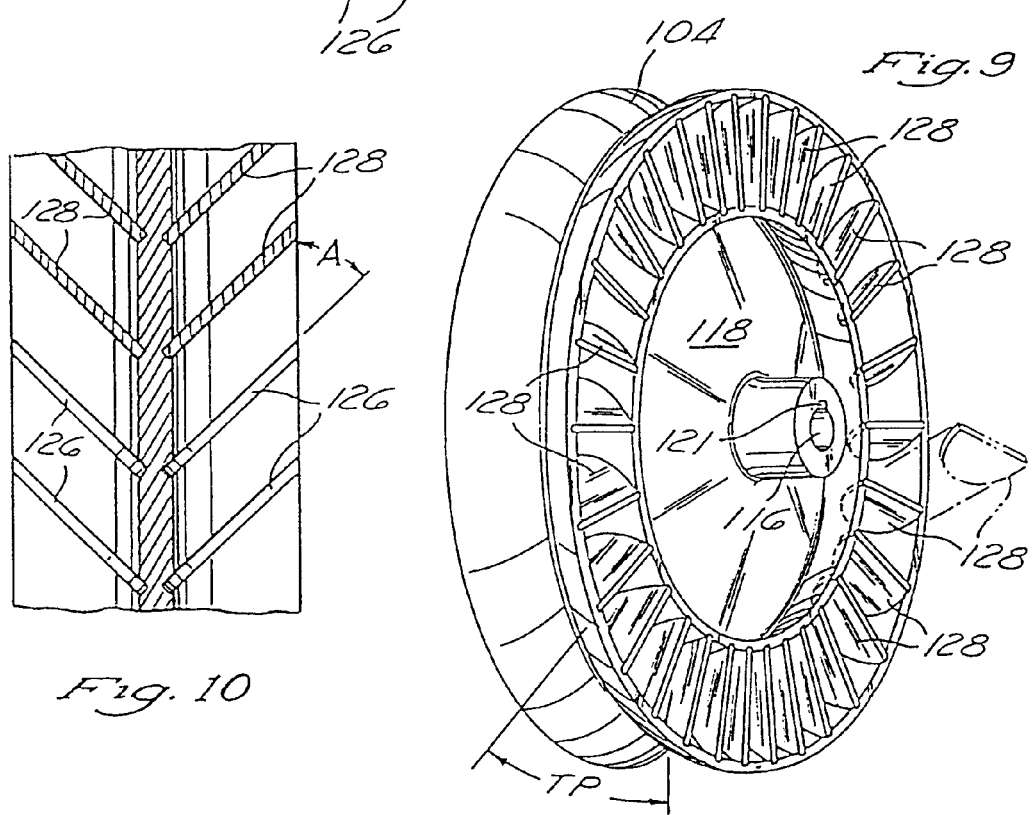
Fig. 10
Fig. 9

PORTABLE DRAG COMPRESSOR POWERED MECHANICAL VENTILATOR

RELATED APPLICATIONS

The present application is a divisional/continuation of U.S. application Ser. No. 10/458,211 entitled PORTABLE DRAG COMPRESSOR POWERED MECHANICAL VENTILATOR filed Jun. 10, 2003, now U.S. Pat. No. 6,877,511 which is a continuation of U.S. application Ser. No. 09/050,555 filed Mar. 30, 1998, now abandoned, which is a continuation of U.S. application Ser. No. 08/794,296 filed Feb. 3, 1997, now U.S. Pat. No. 5,868,133, which is a continuation of U.S. application Ser. No. 08/324,172 filed Oct. 14, 1994, now abandoned.

FIELD OF THE INVENTION

The present invention pertains generally to medical equipment and more particularly to a compressor powered mechanical ventilator device for delivering respiratory ventilation to a mammalian patient.

BACKGROUND OF THE INVENTION

A. Principle of Mechanical Ventilation

In many clinical settings mechanical ventilators are used to facilitate the respiratory flow of gas into and out of the lungs of patients who are sick, injured or anesthetized.

In general, mechanical ventilators provide a repetitive cycling of ventilatory flow, each such repetitive cycle being separated into two phases—an inspiratory phase followed by an expiratory phase.

The inspiratory phase of the ventilator cycle is characterized by the movement of positive-pressure inspiratory flow of gas through the ventilator circuit and into the lungs of the patient. The expiratory phase of the ventilatory cycle is characterized by cessation of the positive pressure inspiratory flow long enough to allow lung deflation to occur. The exhaled gas is vented from the ventilator circuit, typically through an exhalation valve. In patient whose lungs and thoracic musculature exhibit normal compliance, the act of exhalation is usually permitted to occur spontaneously without mechanical assistance from the ventilator.

It is sometimes desirable to control the airway pressure during exhalation to maintain a predetermined amount of positive back pressure during all, or a portion of, the respiratory cycle. Such techniques are often utilized to treat impairments of lung capacity due to pulmonary atelectasis or other factors.

The mechanical ventilators of the prior art have been grouped under various classification schemes, based on various criteria. In general, mechanical ventilators may be grouped or classified according to the parameter(s) which are utilized for a) triggering, b) limiting and c) terminating (e.g., cycling) the inspiratory phase of the ventilator cycle.

"Triggering" is the action that initiates the inspiratory phase of the ventilator cycle. The initiation of the inspiratory phase may be triggered by the ventilator or the patient. The variables and/or parameters which are utilized to trigger the beginning of the inspiratory phase include: time (i.e., respiratory rate), the commencement of spontaneous inhalation by the patient and/or combinations thereof.

"Limiting" of the inspiratory phase refers to the manner in which the inspiratory gas flow is maintained within prescribed ranges to optimize the ventilation of the patient's lungs. The limiting variables and/or parameters are typically controlled by the ventilator, but may change as a result of patient effort and/or physiologic variables such as lung compliance and airway resistance. The variables and/or parameters which are utilized for limiting the inspiratory phase include flow rate, airway pressure and delivered volume.

"Terminating" or "cycling" of the inspiratory phase of the ventilator cycle refers to the point at which the inspiratory flow is stopped and the ventilator and/or patient are permitted to "cycle" into the expiratory phase. Depending on the ventilator control settings, the termination of the inspiratory phase may be brought about by the ventilator or the patient. The variables and/or parameters which are utilized to terminate the inspiratory phase include: time; peak airway pressure; and/or tidal volume ($V_t$).

B. Mechanical Ventilation Modes Utilized in Modern Clinical Practice

In addition Mechanical ventilators are utilized to deliver various "modes" of mechanical ventilation, the particular mode of ventilation being selected or prescribed based on the clinical condition of the patient and the overall objective (i.e., long term ventilation, short term ventilation, weaning from ventilator, etc. . . . ) of the mechanical ventilation.

I. Ventilation Modes i. Intermittent Mandatory Ventilation (IMV)
Intermittent Mandatory Ventilation is a ventilation mode wherein a spontaneously breathing patient receives intermittent mechanical inflation supplied asynchronously by the ventilator.

ii. Synchronized Intermittent Mandatory Ventilation (SMIV)
Synchronized Intermittent Mandatory Ventilation is a ventilation mode wherein a spontaneously breathing patient receives occasional mandatory ventilatory breaths. Mandatory ventilator breaths are synchronized with the patient's spontaneous inspiratory efforts.

iii. Controlled Mechanical Ventilation (CMV)
Controlled Mechanical Ventilation (CMV) is a ventilation mode wherein mechanical breaths are delivered to the patient at time intervals which are unaffected by patient efforts. Controlled Mechanical Ventilation is typically utilized in patients who are not breathing spontaneously.

iv. Assist/Control Ventilation (A/C)
Assist/Control Ventilation (A/C) is a ventilation mode wherein the patient is able to volitionally alter the frequency of mandatory ventilator breaths received, but can not alter the flow and title volume ($V_t$) of each ventilator breath received. Controlled, mandatory breaths are initiated by the ventilator based on the set breath rate. In addition, the patient can demand and trigger an assist breath. After successful triggering of an assist breath, the exhalation valve is closed and gas is delivered to the patient to satisfy the preset tidal volume, peak flow and wave form.

C. Breath Types Utilized in Modern Clinical Practice

Breath types are typically classified according to the particular functions which control:
a) triggering;
b) limiting; and
c) cycling of each breath delivered by the mechanical ventilator, as described and defined hereabove.

Typical breath types and ventilator parameters utilized in modern clinical practice include the following:

i. Machine-Cycled—Mandatory Breath
A machine-cycled, mandatory breath is a breath that is triggered, limited and cycled by the ventilator.

ii. Machine-Cycled—Assist Breath
A machine cycled assist breath is a breath that is triggered by the patient, but is limited and cycled by the ventilator.

iii. Patient-Cycled—Supported Breath
A patient-cycled, supported breath is a breath that is triggered by the patient, limited by the ventilator, and cycled by the patient.

iv. Patient-Cycled—Spontaneous Breath
A patient-cycled spontaneous breath is a breath that is triggered, limited and cycled by the patient. While patient effort limits the flow, and hence the inspiratory volume of the breath, the ventilator may also limit the breath by providing a flow that is to low to maintain a constant pressure in the face of patient inspiratory demand.

v. Volume-Controlled Mandatory Breaths
Volume-controlled breaths are machine-triggered mandatory breaths. The inspiratory phase is initiated by the ventilatory based on a preset breath rate. The inspiratory phase is ended, and the expiratory phase begun, when the breath delivery is determined to be complete based on a preset tidal volume, peak flow and wave form setting. The ventilator remains in expiratory phase until the next inspiratory phase begins.

vi. Volume-Controlled—Assist Breaths
Volume-controlled breaths are machine cycled supported breaths that are initiated by the patient. Volume-controlled assist breaths may be initiated only when the "assist window" is open. The "assist window" is the interval or time during which the ventilator is programmed to monitor inspiratory flow for the purpose of detecting patient inspiratory effort. When a ventilator breath is triggered, the inspiratory phase of such breath will continue until a preset tidal volume peak flow and wave form have been achieved. Thereafter, the exhalation valve is open to permit the expiratory phase to occur. The ventilatory remains in the expiratory phase until the next patient-triggered breath, or the next mandatory inspiratory phase, begins.

vii. Pressure-Controlled Breaths
Pressure-Controlled breaths are delivered by the ventilator using pressure as the key variable for limiting of the inspiratory phase. During pressure control, both the target pressure and the inspiratory time are set, and the tidal volume delivered by the ventilator is a function of these pressure and time settings. The actual tidal volume delivered in each pressure-controlled breath is strongly influenced by patient physiology.

viii. Pressure Support Breaths
Pressure support breaths are triggered by the patient, limited by the ventilator, and cycled by the patient. Thus, each breath is triggered by patient inspiratory effort, but once such triggering occurs the ventilator will assure that a predetermined airway pressure is maintained through the inspiratory phase. The inspiratory phase ends, and the expiratory phase commences, when the patients inspiratory flow has diminished to a preset baseline level.

ix. Sigh Breaths
A sigh breath is a machine-triggered and cycled, volume-controlled, mandatory breath, typically equal to 1.5 times the current tidal volume setting. The inspiratory phase of each sigh breath delivers a preset tidal volume and peak flow. The duration of the inspiratory phase of each sigh breath is limited to a maximum time period, typically 5.5 seconds. The ventilator may be set to deliver a sigh function automatically after a certain number of breaths or a certain time interval (typically 100 breaths for every 7 minutes), which ever interval is shorter. The sigh breath function it may be utilized during control, assist and SIMV modes of operation, and is typically disabled or not utilized in conjunction with pressure controlled breath types or continuous positive air way pressure (CPAP).

x. Proportional Assist Ventilation (PAV)
Proportional Assist Ventilation (PAV) is a type of ventilator breath wherein the ventilator simply amplifies the spontaneous inspiratory effort of the patient, while allowing the patient to remain in complete control of the tidal volume, time duration and flow pattern of each breath received.

xi. Volume Assured Pressure Support (VAPS)
Volume Assured Pressure Support (VAPS) is a type of ventilator breath wherein breath initiation and delivery is similar to a pressure support breath. Additionally, the ventilator is programmed to ensure that a preselected tidal volume ($V_t$) is delivered during such spontaneously initiated breath.

D. Oxygen Enrichment of the Inspiratory Flow

It is sometimes desirable for mechanical ventilators to be equipped with an oxygen-air mixing apparatus for oxygen enrichment of the inspiratory flow. Normal room air has an oxygen content ($FiO_2$) of 21%. In clinical practice, it is often times desirable to ventilate patients with oxygen $FiO_2$ from 21% to 100%. Thus, it is desirable for mechanical ventilators to incorporate systems for blending specific amounts of oxygen with ambient air to provide a prescribed oxygen-enriched $FiO_2$. Typically, volume-cycle ventilators which utilize a volume displacement apparatus have incorporated oxygen mixing mechanisms whereby compressed oxygen is combined with ambient air to produce the selected $FiO_2$ as both gases are drawn into the displacement chamber during the expiratory phase of the ventilator cycle. Nonbellows-type volume-cycled ventilators have incorporated other air-oxygen blending systems for mixing the desired relative volumes of oxygen and air, and for delivering such oxygen-air mixture through the inspirations circuitry of the ventilator.

E. Regulation/Control of Expiratory Pressure

The prior art has included separately controllable exhalation valves which may be preset to exert desired patterns or amounts of expiratory back pressure, when such back pressure is desired to prevent atelectasis or to otherwise improve the ventilation of the patient.

The following are examples of expiratory pressure modes which are frequently utilized in clinical practice:

i. Continuous Positive Airway Pressure (CPAP)
Continuous Positive Airway Pressure (CPAP) is employed during periods of spontaneous breathing by the patient. This mode of ventilation is characterized by the maintenance of a continuously positive airway pressure during both the inspiratory phase, and the expiratory phase, of the patient's spontaneous respiration cycle.

ii. Positive End Expiratory Pressure (PEEP)
In Positive End Expiratory Pressure a predetermined level of positive pressure is maintained in the airway at the end of the expiratory phase of the cycle. Typically, this is accomplished by controlling the exhalation valve so that the exhalation valve may open only until the circuit pressure has decreased to a preselected positive level, at which point the expiration valve closes again to maintain the preselected positive end expiratory pressure (PEEP).

F. Portable Ventilators of the Prior Art

The prior art has included some non-complex portable ventilators which have inherent limitations as to the number and type of variables and/or parameters which may be utilized to trigger, limit and/or terminate the ventilator cycle. Although such non-complex ventilators of the prior art are often sufficiently power efficient and small enough for portable use, their functional limitations typically render them unsuitable for long term ventilation or delivery of complex ventilation modes and or breath types.

The prior art has also included non-portable, complex microprocessor controlled ventilators of the type commonly used in hospital intensive care units. Such ventilators typically incorporate a microcomputer controller which is capable of being programmed to utilize various different variables and/or parameters for triggering, limiting and terminating the inspiratory phase of the ventilator cycle. Complex ventilators of this type are typically capable of delivering many different ventilation modes and or breath types and are selectively operable in various volume-cycled, pressure cycled or time-cycled modes. However, these complex ventilators of the prior art have typically been too large in size, and too power inefficient, for battery-driven portable use. As a result of these factors, most of the complex micro-processor controlled ventilators of the prior art are feasible for use only in hospital critical care units.

As is well known there exist numerous settings, outside of hospital critical care units, where patients could benefit from the availability of a small, battery powered, complex microprocessor controlled mechanical ventilator capable of delivering extended modes of ventilation. For example, critically ill patients sometimes require transport outside of the hospital in various transport vehicles, such as ambulances and helicopters. Also, critical care patients are sometimes transiently moved, within the hospital, from the critical care unit to various special procedure areas (e.g., radiology department, emergency room, catheterization lab etc.,) where they may undergo diagnostic or therapeutic procedures not available in the critical care unit. Additionally, patients who require long term ventilation are not always candidates for admission to acute care hospital critical care units or may be discharged to step-down units or extended care facilities. Also, some non-hospitalized patients may require continuous or intermittent ventilatory support. Many of these patients could benefit from the use of complex microprocessor controlled ventilators, but may be unable to obtain such benefit due to the non-feasibility of employing such ventilators outside of the hospital-critical care unit environment.

In view of the foregoing limitations on the usability of prior art complex microprocessor controlled volume-cycled ventilators, there exists a substantial need in the art for the development of a portable, highly efficient, ventilator capable of programmed delivery of various modern ventilatory modes and breath types, while also being capable of use outside of the hospital critical care unit environment, such as in transport vehicles, extended care facilities and patients homes, etc.

U.S. Pat. No. 4,493,614 (Chu et al.) entitled "PUMP FOR A PORTABLE VENTILATOR" describes a reciprocating piston pump which is purportedly usable in a portable ventilator operable on only internal or external battery power.

U.S. Pat. No. 4,957,107 (Sipin) entitled "GAS DELIVERY MEANS" describes a rotating drag compressor gas delivery system which is ostensibly small enough to be utilized in a portable ventilator. The system described in U.S. Pat. No. 4,957,107 utilizes a high speed rotary compressor which delivers a substantially constant flow of compressed gas. The rotary compressor does not accelerate and decelerate at the beginning and end of each inspiratory phase of the ventilator cycle. Rather, the rotating compressor runs continuously, and a diverter valve is utilized to alternately direct the outflow of the compressor a) into the patients lungs during the inspiratory phase of the ventilation cycle, and b) through an exhaust pathway during the expiratory phase of the ventilation cycle.

Thus, there remains a substantial need for the development of an improved portable mechanical ventilator which incorporates the following features:

A. Capable of operating for extended periods (i.e., at least 2½ hours) using a single portable battery or battery pack as the sole power source;
B. Programmable for use in various different ventilatory modes, such as the above-described IMV, SMV, CMV, PAV, A/C and VPAS.
C. Usable to ventilate non-intubated mask patients as well as intubated patients.
D. Oxygen blending capability for delivering oxygen-enriched inspiratory flow.
E. Capable of providing controlled exhalation back pressure for CPAP or PEEP.
F. Portable, e.g., less than 30 lbs.

SUMMARY OF THE INVENTION

The present invention specifically addresses the above referenced deficiencies and needs of the prior art by providing comprises a mechanical ventilator device which incorporates a rotary compressor for delivering intermittent inspiratory gas flow by repeatedly accelerating and decelerating the compression rotor at the beginning and end of each inspiratory phase. Prior to commencement of each inspiratory ventilation phase, the rotary compressor is stopped, or rotated at a basal rotational speed. Upon commencement of an inspiratory phase, the rotary compressor is accelerated to a greater velocity for delivering the desired inspiratory gas flow. At the end of each inspiratory phase, the rotational velocity of the compressor is decelerated to the basal velocity, or is stopped until commencement of the next inspiratory ventilation phase. A programmable controller is preferably incorporated to control the timing and rotational velocity of the compressor. Additionally, the controller may be programmed to cause the compressor to operate in various modes of ventilation, and various breath types, as employed in modern clinical practice.

Further in accordance with the present invention, there is provided an oxygen blending apparatus which may be utilized optionally with the rotatable compressor ventilation device of the present invention. The oxygen blending apparatus of the present invention comprises a series of valves having flow restricting orifices of varying size. The valves are individually opened and closed to provide a desired oxygen enrichment of the inspiratory gas flow. The oxygen blending apparatus of the present invention may be controlled by a programmable controller associated with, or separate from, the ventilator controller.

Still further in accordance with the invention, there is provided an exhalation valve apparatus comprising a housing which defines an expiratory flow path therethrough and a valving system for controlling the airway pressure during the expiratory phase of the ventilation cycle. A pressure transducer monitors airway pressure during exhalation the output of which is used by the controller to adjust the valving system to maintain desired airway pressure.

In addition the present invention utilizes an exhalation flow transducer to accurately measure patient exhalation flow which may be utilized for determination of exhaled volume and desired triggering of inspiratory flow. In the preferred embodiment, the exhalation flow transducer is integrally formed with the exhalation valve, however, those skilled in the art will recognize that the same can be a separate component insertable into the system. To insure transducer performance accuracy, in the preferred embodiment, the particular operational characteristics of each flow transducer are stored within a memory device preferably a radio-frequency transponder mounted within the exhalation valve to transmit the specific calibration information for the exhalation flow transducer to the controller. Further, the particular construction and mounting of the flow transducer within the exhalation valve is specifically designed to minimize fabrication inaccuracies.

Further objects and advantages of the invention will become apparent to those skilled in the art upon reading and understanding of the following detailed description of preferred embodiments, and upon consideration of the accompanying drawings.

BRIEF DESCRIPTION OF THE DRAWINGS

FIG. 4 is a perspective view of a preferred drag compressor apparatus which may be incorporated into the ventilator system of the present invention.

FIG. 5 is a longitudinal sectional view through line 5-5 of FIG. 4.

FIG. 6 is an enlarged view of a segment of FIG. 5.

FIG. 7 is an enlarged view of a segment of FIG. 6.

FIG. 8 is an elevational view of a preferred drag compressor component of a mechanical ventilator device of the present invention.

FIG. 9 is a perspective view of the drag compressor component of FIG. 8.

FIG. 11a is a longitudinal sectional view of a preferred exhalation valve of the present invention.

FIG. 11b is a perspective view of the preferred spider bobbin component of the exhalation valve shown in FIG. 11a.

FIG. 11c is an exploded perspective view of a portion of the exhalation valve of FIG. 11a.

FIG. 11d is a perspective view of a portion of the exhalation valve shown in FIG. 11c.

FIG. 11e is an exploded perspective view of the preferred flow restricting flapper component of the exhalation valve shown in FIGS. 11a-11d.

DETAILED DESCRIPTION OF THE PREFERRED EMBODIMENT

The following detailed description and the accompanying drawings are provided for purposes of describing and illustrating a presently preferred embodiment of the invention and are not intended to describe all embodiments in which the invention may be reduced to practice. Accordingly, the following detailed description and the accompanying drawings are not to be construed as limitations on the scope of the appended claims.

A. General Description of the Preferred Ventilator System

Figure 1:
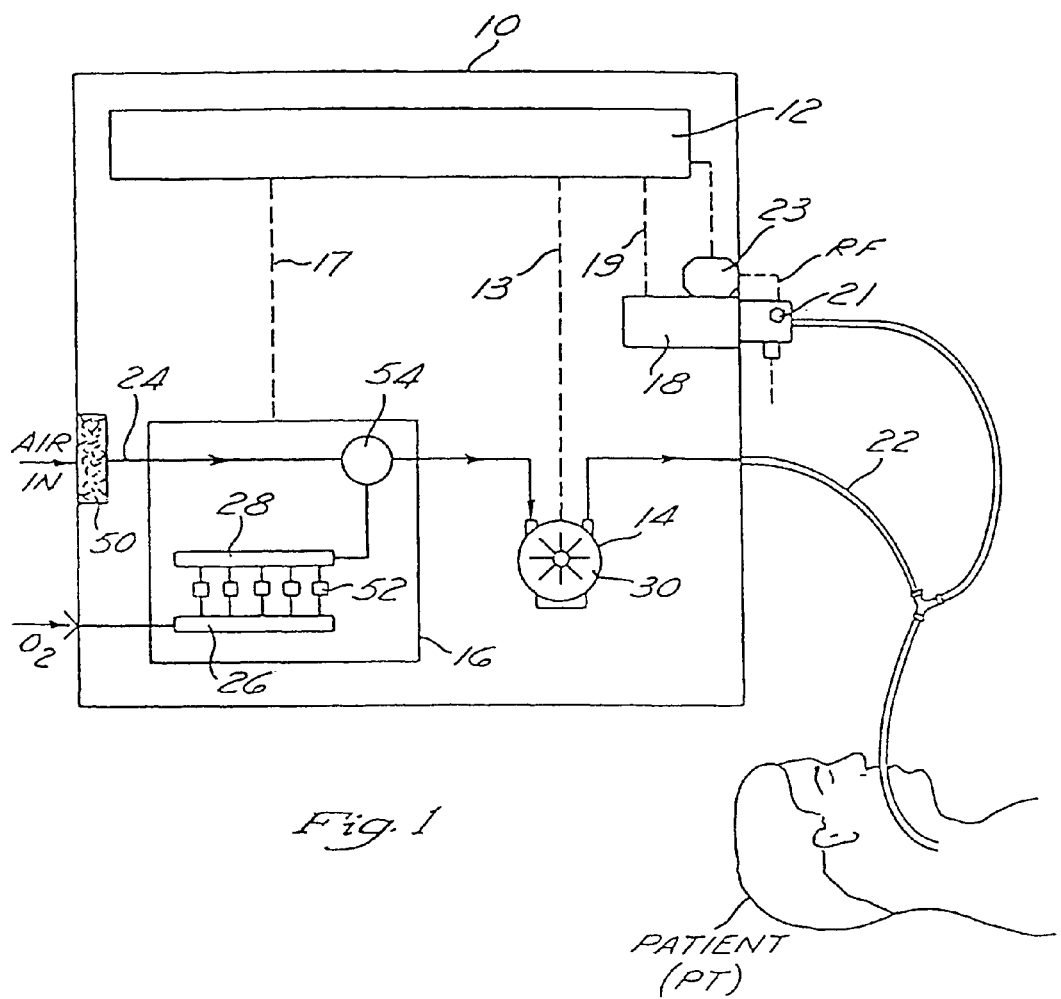
FIG. 1 is a basic schematic diagram of a preferred ventilator system of the present invention incorporating, a) a rotary compressor ventilator device, b) an optional air-oxygen blending apparatus; and c) a controllable exhalation valve, and d) a programmable controller or central processing unit (CPU) which is operative to control and coordinate the functioning of the ventilator, oxygen blending apparatus and exhalation valve.
Figure 2:
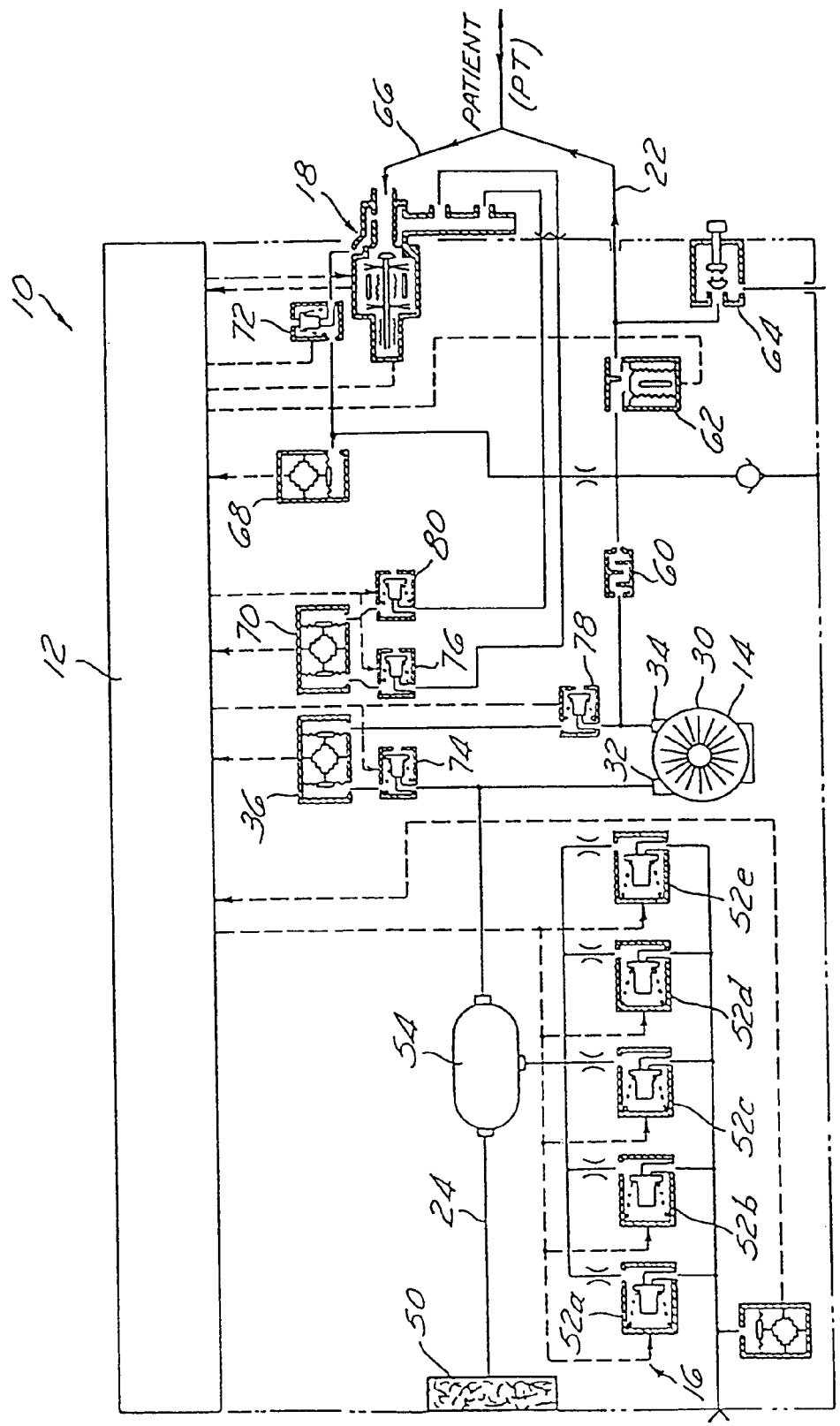
FIG. 2 is a detailed schematic diagram of a ventilator system of the present invention.

With reference to FIGS. 1-2, the mechanical ventilation system 10 of the present invention generally comprises a) a programmable microprocessor controller 12, b) a ventilator device 14, c) an optional oxygen blending apparatus 16 and d) an exhalation valve apparatus 18. Which is preferably implemented as a portable, battery powered system.

The ventilator device 14 incorporates a rotating drag compressor 30 which is driven by an electric motor 102. In response to control signals received from controller 12, a bladed rotor within the compressor 30 will undergo rotation for specifically controlled periods of time and/or, within specifically controlled parameters, so as to provide inspiratory gas flow through line 22 to the patient PT.

Optional oxygen blending apparatus 16 may be utilized to enrich the oxygen content of the inspiratory gas flow provided by the drag compressor ventilator device 14. The preferred oxygen blending apparatus 16 comprises a plurality of (preferably five (5)) solenoid valves 52, each having a specific sized flow restricting orifice. The solenoid valves 52 are arranged in parallel between an oxygen inflow manifold 26 and an oxygen outflow manifold 28. The controller 12 is programmed to open and close the individual solenoid valves 52 for specific periods of time so as to provide a metered flow of oxygen through oxygen outflow manifold 28 and into accumulator 54. Ambient air is drawn through conduit 24 and filter 50, into accumulator 54, where the ambient air combines with the metered inflow of oxygen to provide an oxygen-enriched inspiratory flow containing a prescribed oxygen concentration ($FIO_2$). outflow manifold 28 and into accumulator 54. Ambient air is drawn through conduit 24 and filter 50, into accumulator 54, where the ambient air combines with the metered inflow of oxygen to provide an oxygen-enriched inspiratory flow containing a prescribed oxygen concentration ($FIO_2$).

The presently preferred embodiment of the system 10 will operate when supplied with voltage input within the range of 85-264 VAC at 50/60 Hz.

An AC power cord is preferably connectable to the system 10 to provide AC power input.

Additionally, the system 10 preferably includes an internal battery capable of providing at least 15 minutes, and preferably 30 minutes, of operation. During internal battery operation, some non-essential displays may be dimmed or disabled by the controller 12. The internal battery is preferably capable of being recharged by AC power input provided through the AC power cable, or by a separate battery charger. The internal battery is preferably capable of being fully charged, from a no charged state, within 24 hours. The internal battery charge light 306 shown on the panel of the preferred controller 12a may additionally flash if desired during charging of the internal battery.

Also, the system may include an external battery or battery set capable of providing at least 2 hours of operation, and preferably capable of providing 4 to 8 hours of operation. During external battery use, some non-essential displays may be dimmed or disabled by the controller 12. The battery or battery set is preferably capable of being recharged by delivery of AC power through the AC power cable, or by a separate battery charger. It is preferable that the external battery or battery set be capable of being fully charged, from a no charged state within 24 to 48 hours. The external battery charge light 310 on the panel of the preferred controller 12a may additionally flash if desired during charging of the external battery or battery set.

B. The Preferred Controller Apparatus

It will be appreciated that the controller 12 of the ventilator system 10 of the present invention will vary in complexity, depending on the specific capabilities of the system 10, and whether or not the optional oxygen blending apparatus 16 is incorporated.

Figure 3:
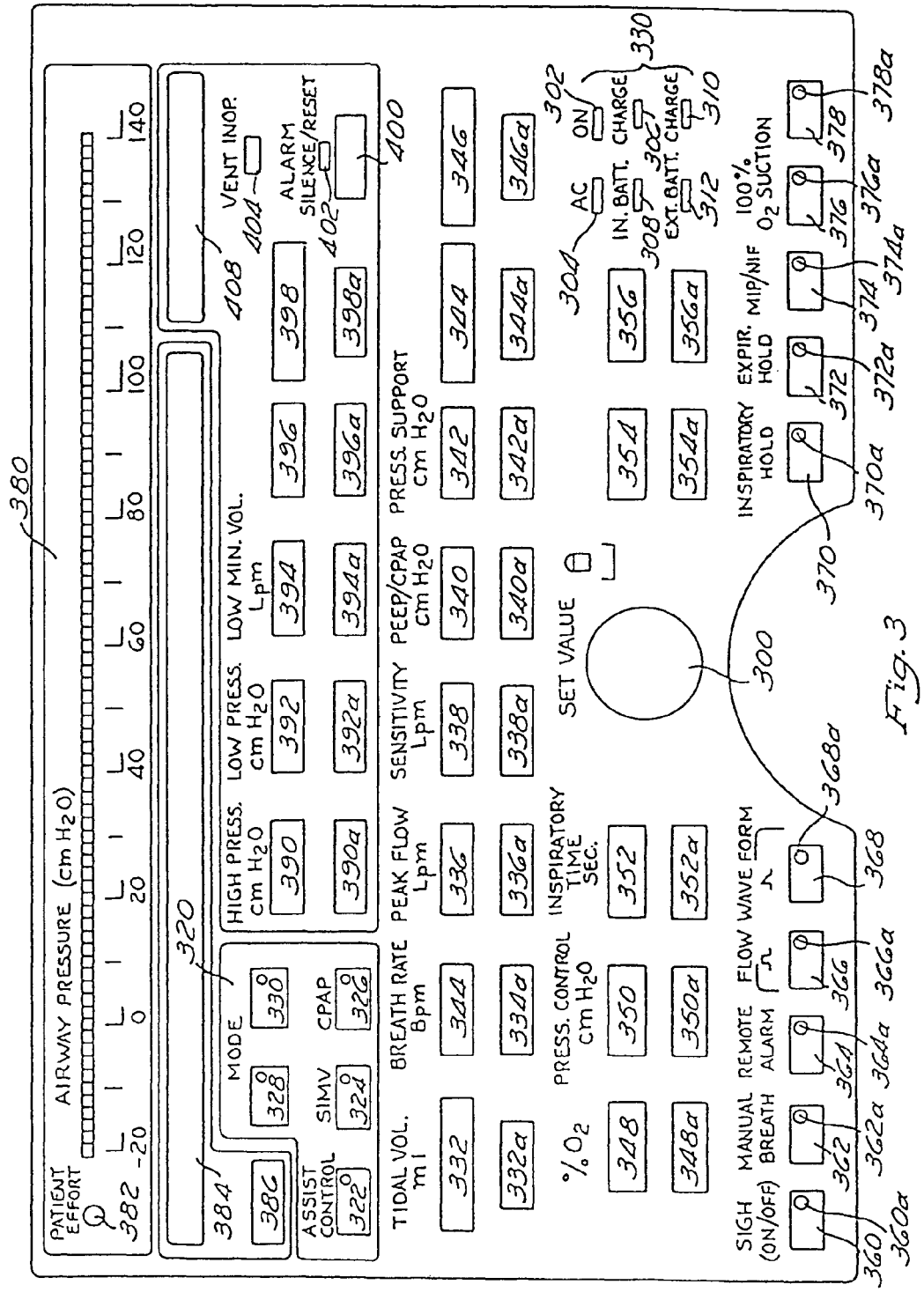
FIG. 3 is a front view of the control panel of a preferred ventilator system of the present invention.

FIG. 3 shows the control panel of a preferred controller apparatus 12a which is usable in connection with a relatively complex embodiment of the ventilatory system 10, incorporating the optional oxygen blending apparatus 16.

Controls Settings and Displays

The specific control settings and displays which are included in the preferred controller 12a, and the ways in which the preferred controller 12a receives and utilizes operator input of specific control settings, are described herebelow:

1. Standby-Off Control

The ventilator system 10 incorporates a stand by/off switch (not shown) which turns the main power on or off. A group of indicator lights 300 are provided on the face panel of the controller 12a, and are more fully described herebelow under the heading "monitors". In general, the panel indicator lights include an "on" indicator 302 which becomes illuminated when the ventilator is turned on. An AC power low/fail indicator light 304 activates when the AC power cord is present and the voltage is out of a specified operating range. Upon sensing low or faulty AC power, the controller 12a will automatically switch the ventilator 14 to internal battery power. The ventilator will continue to operate on internal battery power until such time as power in the internal battery reaches a minimum level. When the power in the internal battery reaches a minimum level, the controller 12a will cause the internal battery light and/or audible alarm 308 to signal that the internal battery is near depletion.

A separate external battery light and/or audible alarm 312 is also provided. The external battery light and/or audible alarm will activate when the external battery is in use, and has a battery voltage which is out of the acceptable operation range. During this condition, the controller 12a will cause all nonessential displays and indicators to shut down.

When AC power is connected to the ventilator 14, but the ventilator is turned off, any internal or external batteries connected to the ventilator will be charged by the incoming AC current. Internal battery charge indicator light 306 and external battery charge indicator light 306 and external battery charged indicator light 310 are provided, and will blink or otherwise indicate charging of the batteries when such condition exists.

2. Mode Select

A mode select module 320 incorporates plural, preferably five (5) mode select buttons 322, 324, 326, 328, 330. Mode select button 322 sets the system 10 for Assist Control (a/c). Mode select button 324 sets the system 10 for Synchronized Intermittent Mandatory Ventilation (SIV). Mode select button 326 sets the system for Continuous Positive Airway Pressure (CPAP).

Spare mode select buttons 328, 330 are provided to permit the controller 12a to be programmed for additional specific ventilation modes such as volume assured pressure support (VAPS) or proportional assist ventilation. When the controller is programmed for additional specific ventilation modes, select buttons 328, 330 may be correspondingly labeled and utilized to set the ventilator 14 to deliver such subsequently programmed ventilation modes.

3. Tidal Volume

A digital tidal volume display 332, with corresponding tidal volume setting button 332a are provided. When tidal volume setting button 332a is depressed, value setting knob 300 may be utilized to dial in a selected tidal volume. The tidal volume display 332 will then provide a digital display of the currently selected tidal volume value.

The typical range of setable tidal volumes is 25 ml-2000 ml.

4. Breath Rate

A digital breath rate display 334, with corresponding breath rate setting button 334a is provided. When breath rate setting button 334a is depressed, value setting knob 300 may be utilized to dial in the desired breath rate. Breath rate display 334 will thereafter display the currently selected breath rate.

The typical rage of selectable breath rates is 0 to 80 breaths per minute.

5. Peak Flow

A digital peak flow display 336, and corresponding peak flow setting button 336a are provided. When peak flow setting button 336a is depressed, value setting knob 300 may be utilized to dial in the desired peak flow. The peak flow display 336 will, thereafter, provide a digital display of the currently selected peak flow.

The typical range of peak flow settings is 10 to 140 liters per minute.

6. Flow Sensitivity

A flow sensitivity digital display 338, and corresponding flow sensitivity setting button 338a are provided. When flow sensitivity setting button 338a is depressed, value setting knob 300 may be utilized to dial in the desired flow sensitivity setting. The flow sensitivity setting display 338 will, thereafter, provide a digital display of the currently selected flow sensitivity setting.

The flow sensitivity setting determines the trigger level for initiation of volume and pressure-controlled assist breaths or pressure support breaths. The initiation of volitional inspiratory effort by the patient creates a change in airway flow as determined by: (turbine bias flow)−(exhalation flow)=patient flow. Triggering occurs when the patient airway flow exceeds the sensitivity setting. The typical range of selectable flow sensitivity settings is from one to ten liters per minute, or off.

Optionally, a fail safe feature may be incorporated whereby, if the patients flow demand does not exceed the flow sensitivity setting, but the airway pressure drops more than 5 $cmH_2O$ below the set PEEP level, and inspiratory cycle will be initiated and a breath will be delivered based on current mode and control settings.

7. PEEP/CPAP

A PEEP/CPAP digital display 340, with corresponding PEEP/CPAP setting button 340a are provided. When PEEP/CPAP setting button 340a is depressed, the value setting knob 300 may be utilized to dial in the desired PEEP/CPAP setting.

The current PEEP/CPAP setting sets the level of pressure in the patient circuit that is maintained between the end of inspiration and the start of the next inspiration. It is also known as the "baseline" pressure.

The preferred range of PEEP/CPAP setting is 0 to 50 cmH$_2$O.

8. Pressure Support

A pressure support digital display 342, and corresponding pressure support setting button 342a, are provided. When pressure support setting button 142a is depressed, value setting knob 300 may be utilized to dial in the desired pressure support setting.

The pressure support setting determines the inspiratory patient circuit pressure during a pressure support breath. This control sets the pressure support level above the baseline setting established by the PEEP/CPAP setting. The total delivered pressure equals the PEEP or CPAP value+pressure support.

The typical range of pressure support settings is from 1 to 60 centimeters of water (cmH$_2$O), or off.

9. FiO$_2$ (% O$_2$)

An FiO$_2$ digital display 348, and corresponding FiO$_2$ setting button 348a, are provided. When the FiO$_2$ setting button 348a is depressed, the value setting knob 300 may be utilized to dial in the desired fractional percentage of oxygen in the air/oxygen gas mixture that is delivered to the patient PT and used for the bias flow. In response to the FiO$_2$ setting, the controller 12 will issue control signals to the oxygen blending apparatus 16 to effect the preset FiO$_2$.

The preferred range of setable FiO$_2$ is between 0.21 and 1.0 (i.e., 21-100 percent oxygen)

10. Pressure Control (Optional)

A pressure control digital display 350, and corresponding pressure control setting button 350a are provided. When the pressure control setting button 350a is depressed, the value setting knob 300 may be utilized to dial in the desired pressure control value.

The pressure control setting enables the system 10 to be utilized for pressure control ventilation, and determines the inspiratory pressure level during delivery of each pressure control breath. The pressure control setting sets the pressure level above any PEEP.

It is preferable that the range of possible pressure control settings be from 1 to 100 cmH$_2$O.

11. Inspiratory Time (Optional)

An optional inspiratory time digital display 352, and corresponding inspiratory time setting button 352a may be provided. When the inspiratory time setting button 352a is depressed, the value setting of 300 may be utilized to dial in the desired inspiratory time.

The set inspiratory time is the time period for the inspiratory phase of a pressure control breath. Thus, this inspiratory time setting is normally usable for pressure control ventilation.

It is preferable that the range of setable inspiratory times being from 0.3 to 10.0 seconds.

12. Additional Displays/Settings

Additional digital displays 344, 346, 354, 356 and corresponding setting buttons 344a, 346a, 354a, 356a are provided to permit the controller 12 to be subsequently programmed or expanded to receive and display additional control settings beyond those which have been described hereabove.

13. Sigh On/Off

A sigh on/off button 360 is provided. When sigh on/off button 360 is depressed, the controller 12 will cause the ventilator 14 to deliver a sigh breath. A sigh breath is a volume-controlled, mandatory breath that is usually equal to 1.5 times the current tidal volume setting shown on tidal volume setting display 332. The sigh breath is delivered according to the current peak flow setting shown on peak flow setting display 336. The inspiratory phase of the sigh breath is preferably limited to a maximum of 5.5 seconds. During a sigh breath, the breath period is automatically increased by a factor of 1.5. The sigh breath function is available during all ventilation modes.

A single depression of the sigh on/off button 348 will cause the ventilator to deliver a volume-controlled sigh breath once every 100 breaths or every 7 minutes, which ever comes first. The sigh breath button 360 includes a visual indicator light 360a which illuminates when the sigh on/off button 360 is depressed and the sigh/breath function is active.

14. Manual Breath

A manual breath button 362 is also provided. Upon depression of the manual breath button 362, the controller 12 will cause the ventilator 14 to deliver a single volume-controlled or pressure-control breath in accordance with the associated volume and/or pressure control settings. An indicator light 362a will illuminate briefly when manual breath button 362 is depressed.

15. Remote Alarm (Optional)

A remote alarm on/off control button 364 is provided to enable or disable the remote alarm. When the remote alarm on/off control button 364 is depressed, indicator light 364a will illuminate. When the remote alarm on/off button 364 is depressed, the remote alarm will be enabled. When this function is enabled, alarm conditions will transmit via hard wire or radio frequency (wireless) to a remote alarm which may be mounted on the outside of a patients room so as to signal attendants outside of the room, when an alarm condition exists.

The specific alarm conditions which may be utilized with the remote alarm function, are described in greater detail herebelow.

16. Flow Waveform (Optional-Applies to Volume Breaths Only)

The controller 12 includes a square flow wave form activation button 366 and a decelerating taper flow wave form actuation button 368. When the square flow wave form actuation button 366 is depressed, indicator light 366a will illuminate, and the ventilator will deliver inspiratory flow at a constant rate according to the peak flow setting, as input and shown on peak flow display 336. When the decelerating paper wave form actuation button 368 is depressed, indicator light 368a will illuminate, and the ventilator will deliver an inspiratory flow which initially increases to the peak flow setting, as input and shown on peak flow display 336, then such inspiratory flow will decelerate to 50 percent of the peak flow setting at the end of the inspiratory phase.

17. Inspiratory Hold (Optional)

An inspiratory hold actuation button 370 is provided, to enable the operator to hold the patient at an elevated pressure following inspiration, so that breath mechanics can be calculated. The length of the delay period is determined by the period of time during which the inspiratory hold button 370 remains depressed, with a maximum limit applied.

18. Expiratory Hold (Optional)

The controller 12 also includes an expiratory hold actuation button 372, which enables the ventilator to calculate auto PEEP. During the expiratory hold, the turbine 30 operation is halted and the exhalation valve 18 remains closed. The difference between the end expiratory pressure, as measured at the end of the expiratory hold period, minus the airway pressure reading recorded at the beginning of the expiratory hold period, will be displayed on monitor window 384.

19. Maximal Inspiratory Pressure/Negative Inspiration Force (Optional)

The preferred controller 12 also incorporates a maximal inspiratory pressure test button 374, to enable the operator to initiate a maximal inspiratory pressure (MIP) test maneuver. This maneuver causes the ventilator to stop all flow to or from the patient. The patient inspiratory effort is then monitored and displayed as MIP/NIF in the monitor window 384.

20. 100% $O_2$ Suction (Optional)

Optionally, the controller 12a includes a 100% $O_2$ actuation button 376 which, when depressed, will cause indicator light 376a to illuminate and will cause the system 10 to deliver an $FiO_2$ of 1.00 (i.e., 100% oxygen) to the patient for a period of three (3) minutes regardless of the current $FiO_2$ setting and/or breath type setting.

This 100% $O_2$ feature enables the operator to selectively deliver 100% oxygen to the patient PT for a three minute period to hyperoxygenate the patient PT prior to disconnection of the patient from the ventilator circuit for purposes of suctioning, or for other clinical reasons.

21. Additional Control Actuation Buttons

An additional control actuation button 378, with indicator light 378a, is provided to enable the controller 12a to be subsequently programmed to perform additional control actuation functions beyond those described hereabove.

Monitors and Indicators

1. AC Power Status Indicator

An AC power indicator light 304 is provided in the face panel of the controller 12 to indicate when sufficient AC power is available and the standby/off switch (not shown) is in the standby position.

2. Internal Battery Status Indicator(s)

An internal battery status indicator light 308 is provided on the panel of the controller 12, and will indicate battery charge level according to predetermined color signals. A separate internal battery charge indicator light 306 may be provided, and will indicate charging status according to predetermined color signals.

3. External Battery Status Indicator(s)

An external battery status indicator light 312 is provided on the panel of the controller 12, and will indicate battery charge level according to predetermined color signals. A separate external battery charge indicator light 310 may be provided, and will indicate charging status according to predetermined color signals.

4. Airway Pressure Monitor

The display panel of the controller 12 includes a real time airway pressure bar graph display 380. A green indicator bar will appear on the airway pressure bar graph display 380 to indicate the real time airway pressure at all times. Red indicators will appear on the airway pressure bar graph to indicate high and low peak pressure alarm setting, as more fully described herebelow under the heading "Alarms". An amber colored indicator will appear on the airway pressure bar graph display 380 to indicate the current PEEP/CPAP setting, Pressure Support setting and/or Pressure Control setting. A patient effort indicator light 382 is located near the airway pressure bar graph display 380, and will illuminate to indicate the occurrence of a patient-initiated breath, including all spontaneous, assist or pressure support breaths.

5. Digital Monitor Display

The panel of the controller 12 preferably includes a digital monitor display 384 and an accompanying monitor select button 386. The controller 12 is programmed to display various monitored parameters. Each time the monitor select button 386 is depressed, the monitored parameters displayed on monitor display 384 will change. The individual parameters may include: exhaled tidal volume, i.e., ratio, mean airway pressure, PEEP, peak inspiratory pressure, total breath rate, total minute ventilation.

Additionally, a display power saving feature may be incorporated, whereby the controller 12 will automatically cause the monitor display 384 to become non-illuminated after a predetermined display period when the system 10 is operating solely on internal or external battery power. Each time the monitor select button 386 is depressed, the display 384 will illuminate for a predetermined period of time only, and then will become non-illuminated. This feature will enable the system 10 to conserve power when the system 10 is being operated solely on internal or external battery power.

Additionally, the controller 12 may be programmed to cause the monitor display 384 to display a special or different group of parameters during a specific operator-initiated maneuver. Examples of special parameter groups which may be displayed during a specific maneuver include the following:

Real-time Pressure (at start of and during all maneuvers)
Plateau Pressure (Inspiratory Hold)
Compliance (Inspiratory Hold)
End Expiratory Pressure (Expiratory Hold)
Auto PEEP (Expiratory Hold)
Maximal Inspiratory Pressure (MIP/NIF)

Alarms and Limits

The preferred controller 12 may be programmed to received operator input of one or more limiting parameters, and to provide audible and/or visual alarm indications when such limiting parameters have been, or are about to be, exceeded.

The visual alarm indicators may comprise steady and or flashing lights which appear on the control panel of the preferred controller 12a.

The audible alarm components will preferably comprise electronic buzzers or beepers which will emit sound discernable by the human ear for a preselected period (e.g., 3 seconds). Preferably, the audible portion of any alarm may be volitionally muted or deactuated by the operator.

Additionally it is preferable that the controller 12 be programmed to automatically reset each alarm if the current ventilation conditions do not fall outside of the preset alarm limits.

Examples of specific limiting parameters and alarm limits which may be programmed into the preferred controller 12, are as follows:

1. High Peak Pressure

The preferred controller 12 includes, on its face panel, a high pressure digital display 390 and a corresponding high pressure alarm limit setting button 390a. When the high pressure alarm limit setting button 390a is depressed, value setting knob 300 may be utilized to dial in a desired high pressure alarm limit value. Such high pressure alarm limit value will then be displayed on high pressure alarm limit display 390.

The currently set high pressure alarm limit, as shown on high pressure alarm limit display 390, will establish the maximum peak inspiratory pressure for all breath types. When the monitored airway pressure exceeds the currently set high pressure alarm limit, audible and visual alarms will be actuated by the controller 12 and the controller will immediately cause the system 10 to cycle to expiratory mode, thereby allowing the airway pressure to return to the baseline bias flow level and along the exhalation valve 18 to regulate pressure at any currently-set peep level.

In order to avoid triggering of the high pressure alarm during delivery of a sigh breath, the controller 12 will be programmed to automatically adjust the high pressure alarm limit value by a factor of 1.5× during the delivery of a sigh breath, provided that such does not result in the high pressure limit value exceeding 140 cmH$_2$O. The controller 12 is preferably programmed not to exceed a high pressure limit setting of 140 cmH$_2$O, even during delivery of a sigh breath.

2. Low Peak Pressure

A low peak airway pressure limit display 392, and corresponding low peak pressure limit setting button 392a, are also provided. When the low peak pressure limit setting button 392a is depressed, value setting knob 300 may be utilized to dial in a desired low peak airway pressure alarm limit value. Such low peak pressure alarm limit value will then be displayed in the low peak pressure display 392.

Audible and/or visual alarms will be activated if the monitored airway pressure fails to exceed the low peak pressure alarm limit setting during the inspiratory phase of a machine-cycled mandatory or assist breath.

The controller 12 is preferably preprogrammed to deactivate the low peak airway pressure alarm during spontaneous, CPAP and pressure support breathing.

The range of low peak pressure settings will preferably be from 2 to 140 cmH$_2$O.

3. Low Minute Volume

A low minute volume display 394, and corresponding low minute volume setting button 394a are provided. When low minute volume setting button 394a is depressed, value setting knob 300 may be used to dial in the desired low minute volume alarm setting. The currently-set low minute volume alarm setting will be displayed in digital display 394.

The controller 12 will be programmed to calculate the current exhaled minute volume based on information received from the exhalation valve differential pressure transducer 70, and to trigger audible and/or visual alarms when the exhaled minute volume becomes less than or equal to the currently set low minute volume alarm limit. This alarm is active for all breath types.

The typical range of setable low minute volume alarm limits is from 0 to 99.9 liters/min.

4. Apnea Alarm

The controller 12 may be programmed to trigger auditory and/or visual apnea alarms when the period between initiation of inspiratory phases exceeds 20 seconds. The controller 12 is preferably also programmed to initiate back-up machine ventilation when an apnea alarm condition exists.

The controller 12 is preferably programmed not to permit volitional silencing of the apnea alarm until the apnea condition has been corrected.

5. Spare Alarm Limit Displays and Setting Buttons

Spare alarm limit displays 396, 398, and corresponding spare alarm limit setting buttons 396a and 398a are provided, to permit the controller 12 to be subsequently expanded or programmed to receive operator input of additional limiting parameters, and to provide auditory and/or visual alarms when such limiting parameters have been exceeded.

6. Ventilator Inoperative

A separate ventilator inoperative light indicator 400 is provided on the face panel of the controller 12. The controller 12 is programmed to cause the ventilator inoperative light to illuminate when predetermined "ventilatory inoperative" conditions exist.

7. AC Power Low/Fail

The controller 12 is preferably programmed to activate visual and/or auditory alarms when an AC power cord is connected to the system 10 and the voltage received by the system 10 is outside of a specified operating range. The controller 12 is preferably also programmed to automatically switch the system 10 to internal battery power under this condition. The AC power low/fail alarm can be silenced, and will remain silenced, until such time as the internal low battery alarm 208 becomes actuated, indicating that the internal battery has become depleted.

8. External/Internal Battery Low/Fail

The controller 12 may be programmed to actuate a visual and or auditory alarm when an external or internal battery is in use, and the battery voltage is outside of an acceptable operating range.

9. O$_2$ Inlet Pressure

The controller 12 may be programmed to provide auditory and/or visual alarms when the oxygen pressure delivered to the system 10 is above or below predetermined limits.

10. Over Pressure Relief Limit

The system 10 includes a mechanical variable pressure relief valve 64, to relieve any over pressurization of the patient circuit.

The range of setable over pressure relief limit values may be between 0 to 140 cmH$_2$O.

Self Testing and Auto Calibration Functions

1. Self Test Function

The preferred controller 12 may be programmed to perform a self-testing function each time the ventilator is powered up. Such self testing function will preferably verify proper functioning of internal components such as microprocessors, memory, transducers and pneumatic control circuits. Such self testing function will also preferably verify that electronic sub-systems are functioning correctly, and are capable of detecting error conditions relating to microprocessor electronics.

Also, during power up, the controller 12 may be programmed to allow a qualified operator who enters a given key sequence, to access trouble shooting and calibration information. In accordance with this feature, the key operator may induce the controller to display, on the monitor display 384, information such as the following:

SOFTWARE REVISION
PEAK FLOW AND PRESSURE TRANSDUCER OUTPUT LAMP TEST/ALL DISPLAYS ON ANY AUTO ZERO AND PURGE FUNCTIONS FOR THE FLOW PRESSURE TRANSDUCER
EVENT DETECTION MENU INCLUDING PREVIOUS STATUS OR FAULT CODES
REMOTE ALARM TEST AND PROGRAM; and
DATA COMMUNICATIONS TEST AND PROGRAM Also, the controller 12 may be programmed to allow a qualified operator who entered a given key sequence, to access a user preference and set up menu. Such menu may include a monitory display 384, of information such as the following:

System lock, enable or disable;
Variable Apnea interval;
Language selection; and
User verification tests.

The user preference and set up menu function may also be accessible during operation of the system 10.

C. A Preferred Rotary Drag Compressor Apparatus

The portable system 10 ventilator of the present invention preferably incorporates a rotary drag compressor apparatus 30 comprising a dual-sided, multi-bladed rotor 104 disposed within a rigid compressor housing 106. An inflow/outflow manifold 108 is formed integrally with the compressor housing 106, and incorporates two (2) inflow passageways 112 and two (2) outflow passageways 110 for channeling gas flow into and out of the compressor apparatus 30.

An electric motor 102, such as a 0.8 peak horsepower, 40 volt D.C. motor, is preferably mounted integrally within the compressor housing 106. Alternatively, the motor 102 may be encased or housed in an encasement or housing which is separate from the compressor housing 106. The motor shaft 114 extends transversely into a bore 116 formed in the central hub 118 of rotor 104. As shown, the bore 116 of the central hub 118 of rotor 104 may include a rectangular key-way 121 formed on one side thereof and the motor shaft 114 may include a corresponding elongate rectangular lug formed thereon. The rectangular lug of the motor shaft 114 inserts within and frictionally engages the key-way 121 of the rotor hub 118, thereby preventing the motor shaft 114 from rotationally slipping or turning within the bore 116 of the rotor hub 118. It will be appreciated however, that various alternative mounting structures, other than the lug and keyway 121 shown in FIGS. 8-9, may be utilized to rotatably mount the motor shaft 114 to the rotor 104.

The rotor hub 118 is preferably formed having a concave configuration, as shown in FIG. 5. Such concave configuration serves to impart structural integrity and strength to the rotor 104, without significantly increasing the mass of the rotor 104 as would result from the formation of additional strengthening ribs or bosses on the rotor hub 118.

As shown in FIGS. 5-10, a first annular trough 120 extends about the periphery of the front side of the rotor 104, and a second annular trough 122 extends about the periphery of the backside of the rotor 104.

A multiplicity of rotor blade-receiving slots 126 are formed angularly, at evenly spaced intervals about the inner surfaces of the first 120 and second 122 annular troughs. Rotor blades 128 are mounted at spaced-apart locations around each annular trough 120, 122 such that the radial peripheral edge 127 of each blade 128 is inserted into and resides within a corresponding blade receiving slot 126 and the leading edge 129 of each blade traverses across the open annular trough 120 or 122, as shown. Each blade 128 is affixed by adhesive, or other suitable means, to the body of the rotor 104.

In the preferred embodiment the blades 128 are located in axially aligned positions, i.e., non-staggered directly opposite positions on opposite sides of the rotor 104 so as to promote even pressure balance and symmetrical weight distribution within the rotor 104.

The rotor 104 is rotatably mounted within the compressor housing 106 such that the first 120 and second 122 annular cavities are in alignment with the inflow 110 and outflow 112 channels, as shown.

In order to optimize the controllability of the rotor 104 velocity, and to minimize the wear or stress on the system drive components from repeated abrupt starting and stopping of the rotor 104, it is desirable that the overall mass of the rotor 104 be minimized. Toward this end, the body of the rotor 104 is preferably constructed of light weight material such as aluminum, and the individual blades 128 of the rotor 104 are preferably constructed of light weight material such as glass-filled epoxy. In embodiments where the body of the rotor 104 is formed of aluminum and the blades 128 are formed of glass-filled epoxy, a suitable adhesive such as epoxy may be utilized to bond the radial edges of the blades 128 within their corresponding blade-receiving slots 126. Alternatively, it is contemplated to form the rotor and blades integrally, as by way of a molding process whereby metal (e.g., aluminum), polymer or composite materials are molded to form the blades 128 and rotor 104 as a unitary structure.

Figure 10:
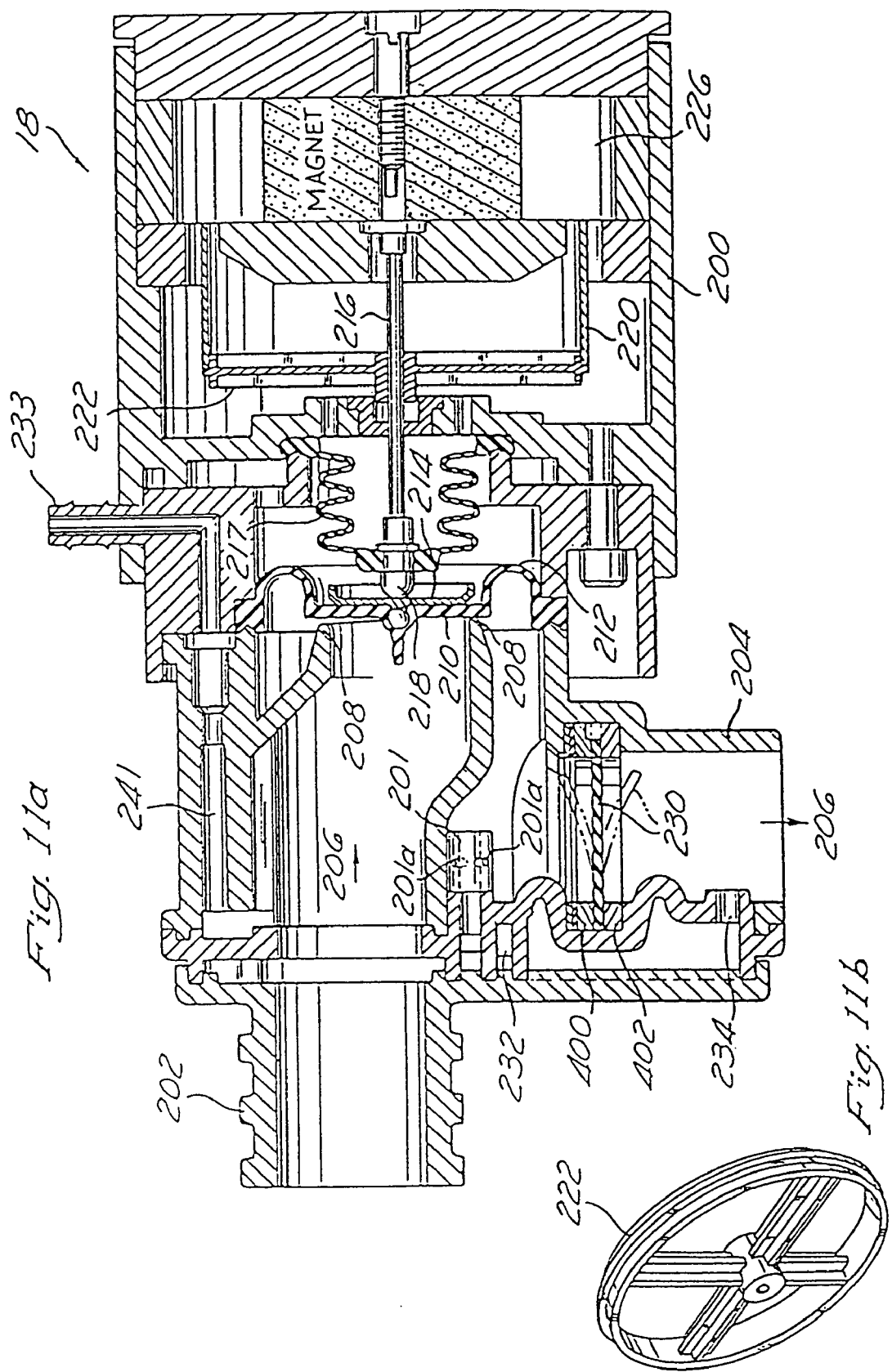
FIG. 10 is an enlarged view of a segment of FIG. 9.

After the rotor blades 128 have been mounted and secured in their respective blade-receiving slots 126, each individual blade 128 will preferably be disposed at an angle of attack A, relative to a flat transverse plane TP projected transversely through the body of the rotor 104, between the first annular trough 120 on the front side of the rotor 104, and the second annular trough 122 on the backside of the rotor 104. The angle A is preferably in the range of 30-60 degrees and, in the preferred embodiment shown in FIGS. 8-10 is 55 degrees. Such angle A is selected to provide optimal flow-generating efficiency of the rotor 104.

Figure 12:
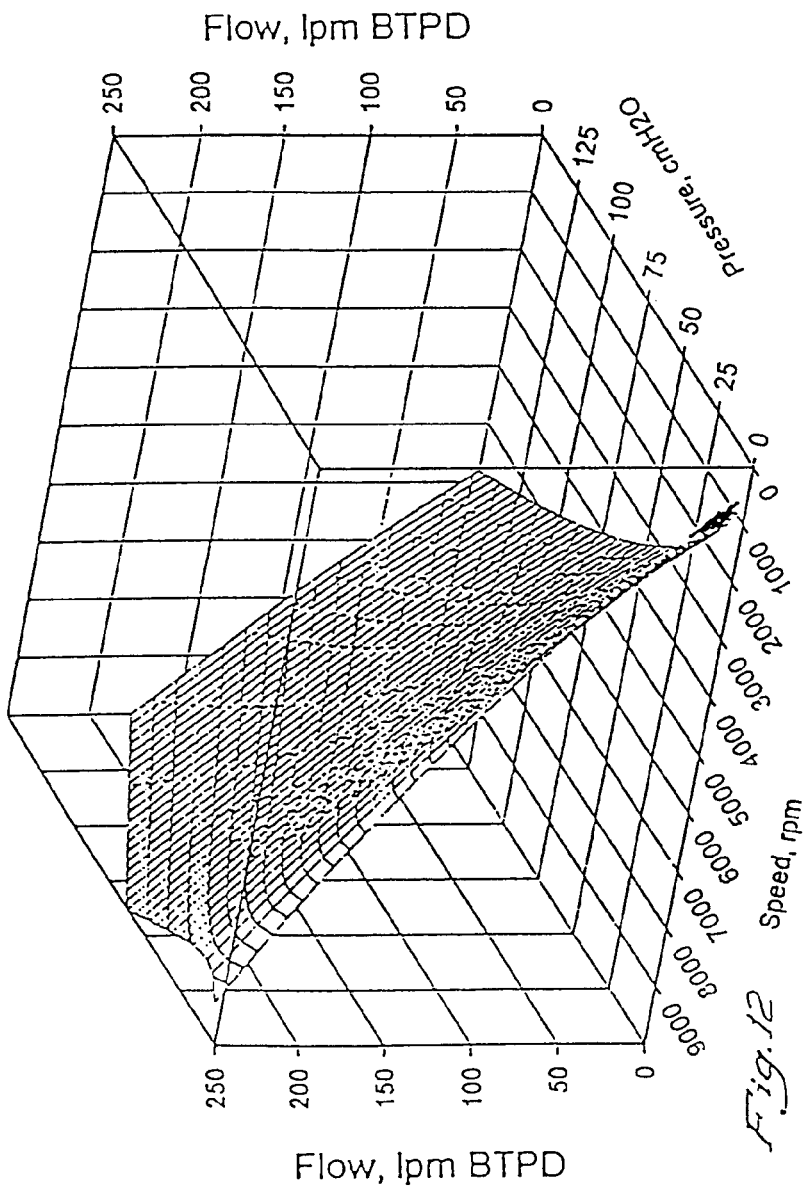
FIG. 12 is a graphic example of flow vs. speed vs. pressure data generated for a preferred exhalation valve of the present invention, accompanied by an exhalation valve characterization algorithm computed therefrom.

In operation, it is necessary to precisely control the timing of the acceleration, deceleration, and the rotational speed, of the rotor 104 in order to generate a prescribed inspiratory pressure and/or flow rate and/or volume. Although standard manufacturing tolerances may be maintained when manufacturing the rotor 104 and other components of the compressor 30 (e.g., the rotor 104, compressor housing 106, motor 102) each individual compressor 30 will typically exhibit some individual variation of flow output as a function of the rotational speed and differential pressure of that compressor 30. Thus, in order to optimize the precision with which the inspiratory flow may be controlled, it is desirable to obtain precise flow and pressure data at various turbine speeds for each individual compressor 30, and to provide such characterization data to the controller 12 to enable the controller 12 to adjust for individual variations in the pressure and/or flow created by the particular compressor 30 in use. As a practical matter, this may be accomplished in either of two ways. One way is to generate discrete flow rate, speed and pressure measurements for each compressor 30 at the time of manufacture, and to provide a table of such discreet flow rate, speed and pressure values to the ventilator controller 12 at the time the particular compressor 30 is installed. The controller 12 will be correspondingly programmed to perform the necessary interpolative mathematical steps to obtain instantaneous flow, speed or pressure determinations as a function of any two such variables, for the particular compressor 30. The second way is to experimentally generate a series of flow, speed and pressure data points over a range of normal operating rotor speeds, and to subsequently derive a unique speed vs. flow vs. pressure equation to characterize each individual compressor 30. Such individual characterization equation is then programmed into, or otherwise provided to, the controller 12 and the controller 12 is programmed to utilize such equation to compute precise, instantaneous speed, flow rate and pressure control signals for controlling the individual compressor 30 in use. An example of such graphical speed vs. flow rate vs. pressure data, and a characterization equation derived therefrom, is shown in FIG. 12.

Given the current cost of microprocessor technology, providing a controller 12 which has the capability to receive and process such a characterization equation as shown in (FIG. 12) for controlling the compressor 30 would require substantial expense and size enlargement of the controller 12. Accordingly, given the present state of the art, it is most desirable to utilize the former of the two above-described methods—that is, providing a database of discrete flow, speed and pressure values and programming of the controller 12 to perform the necessary mathematical interpolations of the provided data points for maintaining compressor-specific control of the pressure, flow rate and/or volume of gas provided in each inspiratory phase at the ventilation cycle. The experimentally generated database of discreet flow, speed and pressure valves may be encoded onto an EPROM or any other suitable database storage device. Such EPROM or other database storage device may be located on or within the compressor 30 itself and communicated to the controller 12 via appropriate circuitry. Alternatively, such EPROM or database storage device may be installed directly into the controller 12 at the time the particular compressor 30 is installed within the ventilator device 14.

The controlled inspiratory flow generated by the rotary drag compressor 30, exists from the compressor outlet 34 and through line 22 to the patient PT. As shown in FIG. 2, an output silencer 60, such as a hollow chamber having a quantity of muffling material formed therearound, is preferably positioned on inspiratory flow line 22 to reduce the sound generated by the ventilator 14 during operation. An inspiration occlusion valve 62 is additionally preferably mounted on inspiratory flow line 22 to accomplish operator controlled stoppage of the inspiratory flow as required during performance of a maximal inspiratory force maneuver. Additionally, a pressure relief valve 64 is connected to inspiratory flow line 22 to provide a safeguard against delivering excessive inspiratory pressure to the patient PT. The pressure relief valve 64 may be manually set to the desired limit pressure, by the operator.

In general, the rotary drag compressor ventilator 14 operates by periodic rotating of the rotor 130 within the compressor 30 to generate the desired inspiratory gas flow through line 22. It is desirable that the rotor 130 be accelerated and decelerated as rapidly as possible. Such rapid acceleration/deceleration is facilitated by a reduction in inertial effects as a result of the above-described low mass construction of the rotor 104. The speed and time of rotation of the rotor 104, during each inspiratory phase of the ventilator cycle, is controlled by the controller 12 based on the variables and/or parameters which have been selected for triggering, limiting and terminating the inspiratory phase.

The precise flow, volume or pressure delivered through the inspiratory line 22 is controlled by the controller based on the EPROM-stored compressor characterization data received by the controller, as well as periodic or continuous monitoring of the rotational speed of the rotor 104 and the change in pressure ($\Delta_P$) between the inlet side 32 and outlet side 34 of the compressor 30 as monitored by the differential pressure transducer 36.

In the presently preferred embodiment, the controller 12 is programmed to deliver breaths by either of two available closed loop algorithms; volume or pressure.

Example

Volume Breaths

Prior to Volume breath initiation, the controller 12 generates a predefined command waveform of flow vs time. The waveform is generated using the current Flow, Volume and Waveform input settings from the front panel. Since the mathematical integral of flow over time is equal to the volume delivered, the controller can determine the appropriate inspiratory time. Once a volume breath has been triggered, the controller uses closed loop control techniques well known in the art to drive the compressor, periodically read the compressor differential pressure and rotational speed, and then calls upon the specific stored compressor characterization data to arrive at the actual flow rate. Once actual flow rate is known, it is compared or "fed back" to the current commanded flow, and a resulting error is derived. The error is then processed through a control algorithm, and the compressor speed is adjusted accordingly to deliver the desired flow rate. This process is repeated continuously until the inspiration is complete.

Example

Pressure Breaths

Pressure breaths include several breath types such as Pressure Support or Pressure Control. In these breath types, the controller commands the compressor to provide flow as required to achieve a pressure as input from the front panel.

Once a pressure breath has been triggered, the controller uses closed loop control techniques well known in the art to drive the compressor 30 and to achieve the desired patient airway pressure. The controller periodically reads the actual airway pressure. Once actual pressure is known, it is "fed back" and compared to the current commanded pressure, and a resulting error is derived. The error is then processed through a control algorithm, and the compressor speed is adjusted accordingly to deliver the desired pressure. This process is repeated continuously until the inspiration is complete.

For both breath types, once the selected inspiratory termination variable is reached, the controller will signal the compressor motor 102 to stop or decelerate to a baseline level, thereby cycling the ventilator in to the expiratory phase.

D. A Preferred Oxygen Blending Apparatus

When oxygen enrichment of the inspiratory flow is desired, the controller 12 may be additionally programmed or equipped to control the operation of the oxygen blending apparatus 16 to mix a prescribed amount of oxygen with ambient air drawn through air intake 24, thereby providing an inspiratory flow having a prescribed oxygen content ($FiO_2$) between 21%-100%.

As shown in FIGS. 2 and 3, the preferred oxygen blending apparatus 16 comprises an air inlet line 24 which opens into a hollow vessel or accumulator 54.

Oxygen inlet line 26 is connected to a pressurized source of oxygen and leads, via a manifold to a series of solenoid valves 52. Although not by way of limitation, in the preferred embodiment as shown in FIG. 3, five (5) separate solenoid valves 52a-52e are utilized. Each such separate solenoid valve 52a-52e has a specific (usually differing) sized flow restricting orifice formed therein so that each such solenoid valve 52a-52e will permit differing amounts of oxygen to pass into accumulator 54, per unit of time during which each such solenoid valve 52a-52e is maintained in an open position. The controller 12 is preprogrammed to determine the specific period(s) of time each solenoid valve 52a-52e must remain open to provide the necessary amount of oxygen to accumulator 54 to result in the prescribed oxygen concentration ($FiO_2$).

Algorithm for a Preferred Oxygen Blending Apparatus

The rotational velocity of the rotor 104 and differential pressure across the inflow/outflow manifold 108 are measured by the controller 12 and from this data the controller 12 is able to determine the flow of gas through the compressor 30 from the accumulator 54. The controller 12 integrates the air flow drawn through the compressor 30 to determine the accumulated volume of enriched gas drawn from said accumulator 54. In order to maintain the flow of gas at the prescribed $FiO_2$ level, a portion of this removed volume must be replaced in the accumulator 54 with pure oxygen.

The accumulated volume is compared to a predetermined trigger volume for each of the solenoids 52a-52e, which in the preferred embodiment, is defined by the equation:

Trigger Volume=
(Solenoid Flow*Time*79)/[(FiO$_2$-21)*2]

Starting with the smallest, each solenoid that is not currently open is compared. When the accumulated volume reaches the trigger volume for a solenoid 52, the controller 12 opens that solenoid 52 for a period of time allowing oxygen to flow from the oxygen inlet line 26 through the solenoid 52 and into the accumulator 54. The controller 12 then adjusts the accumulated volume appropriately by subtracting a volume, proportional to the volume of oxygen delivered to the accumulator 54 from the accumulated volume defined by the equation:

Subtracted Volume=
(Solenoid Flow*Time*79)/(FiO$_2$-21).

This process is repeated continuously.

The trigger volume the controller 12 uses to open an individual solenoid 52a-52e is independent for each solenoid 52 and is function of the flow capacity of the particular solenoid 52a-52e, the prescribed FiO$_2$ level, and the amount of time the solenoid 52 is open. In the preferred embodiment, the amount of time each solenoid 52 is open is the same for each solenoid 52, but may vary as a function of oxygen inlet pressure.

Example

Delivery of 0.6 Fio$_2$ Using 4 Solenoids

In this example, the oxygen blending apparatus has 4 solenoids with flows of 5 lpm, 15 lpm, 40 lpm, and 80 lpm respectively. The FiO$_2$ setting is 60%, thus the trigger volumes for each of the 4 solenoids is 8 ml, 25 ml, 66 ml, and 133 ml respectively. Furthermore a constant oxygen inlet pressure is assumed resulting in an "on" time of 100 ms for the solenoids, a constant compressor flow of 60 lpm, and a period of 1 ms. The following table describes the state of the oxygen blending algorithm after various iterations:

| Time (ms) | Accumulated Volume (ml) | Solenoid 1 (8 ml) | Solenoid 2 (25 ml) | Solenoid 3 (66 ml) | Solenoid 4 (133 ml) |
|---|---|---|---|---|---|
| 0 | 0 | off | off | off | off |
| 1 | 1 | off | off | off | off |
| 2 | 2 | off | off | off | off |
| ** | | | | | |
| 7 | 7 | off | off | off | off |
| 8 | 0 | on | off | off | off |
| 9 | 1 | on | off | off | off |
| ** | | | | | |
| 32 | 24 | off | off | off | off |
| 33 | 0 | on | on | off | off |
| 34 | 1 | on | on | off | off |
| ** | | | | | |
| 98 | 65 | on | on | off | off |
| 99 | 0 | on | on | on | off |
| 100 | 1 | on | on | on | off |
| ** | | | | | |
| 107 | 8 | on | on | on | off |
| 108 | 1 | off > on* | on | on | off |

*At 108 ms the 8 ml solenoid turned off after having been on for 100 ms, but since the accumulated volume is now 9 ml the solenoid is turned on again.

Thus, by independently operating the four (4) separate solenoids as shown in the above table, a 0.6 FiO$_2$ is consistently delivered through the compressor 30.

E. A Preferred Exhalation Valve and Exhalation Flow Transducer

Referring generally to FIGS. 11a-11e the preferred exhalation valve and exhalation flow transducer assembly of the present invention is depicted. By way of overview, the exhalation valve 18 comprises a housing which defines an expiratory flow path therethrough and a valving system for controlling the airway pressure during the expiratory phase of the ventilation cycle. The exhalation valve 18 shares numerous structural and functional attributes with the exhalation valve described in U.S. Pat. No. 5,127,400 (DeVries et al) entitled Ventilator Exhalation Valve, issued Jul. 7, 1994, the disclosure of which is expressly incorporated herein by reference.

In addition, the exhalation valve assembly 18 of the present invention additionally incorporates an exhalation flow transducer 230 which serves to monitor exhalation flow from the patient and generates an output signal to the controller 12. The output signal is then utilized by the controller to determine when patient exhalation has ceased to thereby initiate inspiratory flow to the patient. In the preferred embodiment, the exhalation flow transducer 230 is mounted within the exhalation valve 18 in unique structure to minimize manufacturing inaccuracies. Further, in the preferred embodiment, the particular operational characteristics of the exhalation flow transducer 230 are stored within a memory device which is then communicated to the controller 12 to insure accuracy in flow measurements. The exhalation flow transducer 230 of the present invention shares numerous structural and functional attributes with the flow transducer described in the U.S. Pat. No. 4,993,269, issued to Guillaume et al., entitled Variable Orifice Flow Sensing Apparatus, issued on Feb. 19, 1991, the disclosure of which is expressly incorporated herein by reference.

Referring more particularly to FIGS. 11a through 11e, the exhalation valve 18 of the present invention is formed having a housing 200 including an exhalation tubing connector 202 formed at a first location thereon and an outflow port 204 formed at a second location thereon. An exhalation gas flow passageway 206 extends through the interior of the housing 200 such that expiratory gas may flow from the exhalation tubing connector 202 through the exhalation passageway 206 within the interior of the exhalation valve 18 and subsequently passed out of the outflow port 204. Midway through the expiratory flow passageway 206, there is formed an annular valve seat 208. The annular valve seat 208 may be disposed in a plane which is parallel to the plane of the flat diaphragm 210 or alternatively, as in the embodiment shown, the annular valve seat 208 may be slightly angled or tapered relative to the plane in which the flat diaphragm 210 is positioned. Such angling or tapering of the valve seat 208 facilitates seating of the diaphragm 210 on the valve seat 208 without flutter or bouncing of the diaphragm 210. The elastomeric disc or diaphragm 210 is configured and constructed to initially contact the farthest extending side of the angled valve seat 208, and to subsequently settle or conform onto the remainder of the angled valve seat 208, thereby avoiding the potential for flutter or bouncing which may occur when the diaphragm 210 seats against a flat non-angled valve seat 208.

The disc or diaphragm 210 is preferably attached to the surrounding rigid housing 200 by way of an annular flexible frenulum 212. Frenulum 212 serves to hold the disc or diaphragm 210 in axial alignment with the annular valve seat 208, while permitting the disc or diaphragm 210 to alternatively move back and forth between a closed position wherein the diaphragm 210 is firmly seated against the valve seat 208 (FIG. 11a) and a fully open position wherein the disc or diaphragm 210 is retracted rearwardly into the adjacent cavity within the housing 200 thereby providing an unrestricted flow path 206 through which expiratory gas may flow.

A pressure distributing plate 214 is mounted on the backside of the diaphragm 210. A hollow actuation shaft 216 is mounted within the housing 200 and is axially reciprocal back and forth to control the position of the diaphragm 210 relative the valve seat 208. A bulbous tip member 218 is mounted on the distal end of a hollow actuation shaft 216. A corresponding pressure distribution plate 214 is mounted on the back of the diaphragm 210. Forward movement of the actuation shaft 216 causes the bulbous tip member 218 to exert forward pressure against the plate 214 thereby forcing the diaphragm 210 toward its closed position. When the actuation shaft 216 is in a fully forward position, the diaphragm 210 will be held in firm abutment against the annular valve seat 208 thereby terminating flow through the passage 206. Conversely when the actuation shaft 216 is retracted, the diaphragm 210 moves away from the valve seat 208 thereby allowing flow through the passageway 206 thereby allowing flow through the passageway 206.

The movement of the shaft 216 is controlled by way of an electrical induction coil 220 and spider bobbin 222 arrangement. In the preferred embodiment, the electrical induction coil 220 is formed without having an internal support structure typically utilized in induction coils so as to minimize inertial concerns. In this regard, the coil 220 is typically formed by winding upon a mandrel and subsequently maintained in this wound configuration by way of application of a suitable binder or varnish. Additionally, in the preferred embodiment, the bobbin 222 is preferably formed having a cross-beam construction, as shown in FIG. 11b, to decrease the mass of the bobbin 222 while maintaining its structural integrity. Similarly, the shaft 216 is preferably formed from a hollow stainless steel material so as to be relatively strong yet light weight enough for minimizing inertial concerns.

As shown, the bobbin 222 is affixed to the distal end of the induction coil 220 and the shaft 216 extends through an aperture formed in the center of the bobbin and is frictionally or otherwise affixed to the bobbin such that the shaft 216 will move back and forth in accordance with the bobbin 222 and coil 220. As the current passing into the induction coil 220 increases, the coil 220 will translate rearwardly into the coil receiving space 226 about the magnet thereby moving the shaft 216 and blunt tip member 218 in the rearward direction and allowing the diaphragm 210 to move in an open position away from the valve seat 208 of the expiratory flow path 206. With the diaphragm 210 in such open position, expiratory flow from the patient PT may pass through the expiratory flow pathway 206 and out the expiratory port 204.

Conversely, when the expiratory flow has decreased or terminated, the current into the induction coil may change direction, thereby causing the induction coil to translate forwardly. Such forward translation of the induction coil 220 will drive the bobbin 222, shaft 216, and bulbous tip member 218 in a forward direction, such that the bulbous tip member 218 will press against the flow distributing plate 214 on the backside of the diaphragm 210 causing the diaphragm to seat against the valve seat 208. With the diaphragm 210 seated against the valve seat 208, the inspiratory phase of the ventilator cycle may begin and ambient air will be prevented from aspirating or backflowing into the patient circuit through the exhalation port 204.

In the preferred embodiment, a elastomeric boot 217 or dust barrier is mounted about the distal portion of the hollow actuation shaft 216, and is configured and constructed to permit the shaft 216 to freely move back and forth between its fully extended closed position and a fully retracted open position while preventing dust or moisture from seeping or passing into the induction coil 220.

Figure 11:
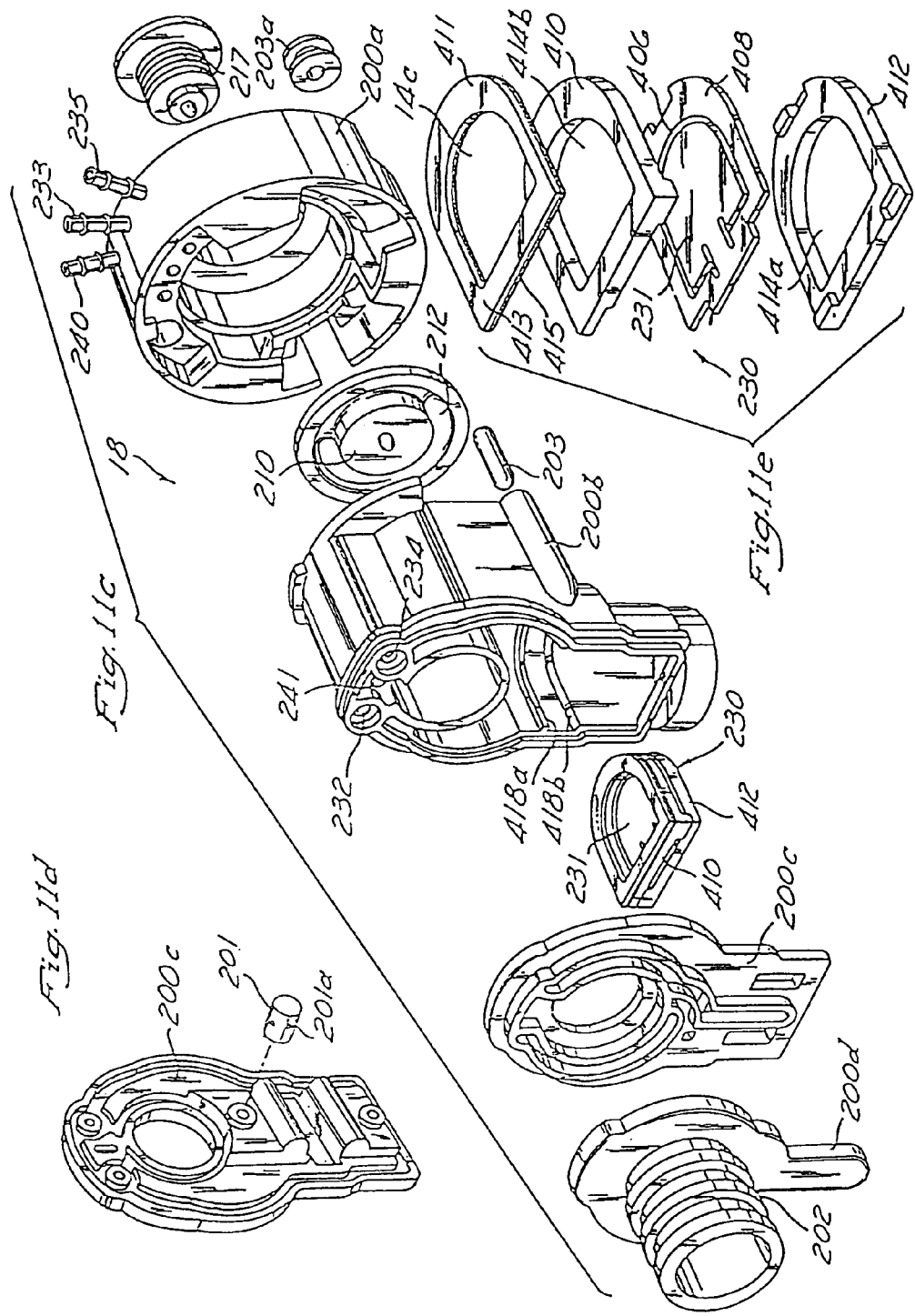

As best shown in FIG. 11, FIGS. 11a and 11c, the housing of the exhalation valve 18 includes a frontal portion formed by the housing segments 200b, 200c, and 200d. An airway pressure passage 241 is provided within the housing portion 200b, which enables the pressure within the exhalation passageway 206 to be communicated to an airway pressure tubing connector 233. Airway pressure tubing connector 233 is connected via tubing to an airway pressure transducer 68 (shown in FIG. 2) which monitors airway pressure and outputs a signal to the controller 12. Based upon desired operating conditions, the controller 12, in response of receipt of the pressure signal from pressure transducer 68 increases or decreases the voltage applied to the coil 220 to maintain desired pressure within the exhalation air passage 206. As will be recognized, such monitoring of the airway pressure is continuous during operation of the ventilator cycle.

As previously mentioned, the exhalation flow transducer 230 of the present invention is preferably disposed with the exhalation valve housing and serves to monitor exhalation flow from the patient PT. More particular, the exhalation flow transducer 230 of the present invention preferably incorporates a feedback control system for providing real time monitoring of the patient's actual expiratory flow rate. As best shown in FIGS. 11a and 11c, the expiratory flow transducer 230 of the present invention is incorporated within the exhalation flow path 206 within housing segment 200b. The flow transducer 230 is preferably formed from a flat sheet of flexible material having a cut out region 406 formed therein. A peripheral portion 408 of the flat sheet exists outside of the cut out region 406 and flapper portion 231 is defined within the cut out region 406. Frame members 410 and 412 preferably formed of a polymer material, are mounted on opposite sides of the flat sheet so as to exert inward clamping pressure on the peripheral portion 408 of the flat sheet. The flapper portion 231 of the flat sheet is thus held in its desired transverse position within the open central aperture 14a and 14b of the transducer assembly, and such flapper portion 231 is thus capable of flexing downstream in response to exhalation flow.

To minimize the inducement of stresses within the flow transducer assembly 230, a frame member 411 is preferably positioned in abutting juxtaposition to the outboard surface of at least one of the frame members 410, 412. In the preferred embodiment shown in FIG. 11c, the frame member 411 is positioned in abutment with the upper frame member 410. Such frame member 411 comprises a metal frame portion 413 and includes an elastomeric cushioning gasket or washer 415 disposed on the lower side thereof. A central aperture 14c is formed in the frame member 411, such aperture 14c being of the same configuration, and in axial alignment with central apertures 14a, 14b of the upper and lower frame members 410, 412.

Upper and lower abutment shoulders 418a, 418b, are formed within the exhalation valve housing 200 to frictionally engage and hold the flow transducer assembly 230 in its desired operative position. When so inserted, the upper engagement shoulder 418a will abut against the upper surface of the frame member 411, and the lower abutment shoulder 418b will abut against the lower surface of the lower frame member 412, thereby exerting the desired inward compressive force on the flow transducer assembly 230. As will be recognized, the inclusion of the cushioning washer 415 serves to evenly distribute clamping pressure about the peripheral portion 408, thereby minimizing the creation of localized stress within the flow transducer 230.

When the transducer assembly 230 is operatively positioned between the upper and lower abutment shoulders 418a, 418b, an upstream pressure port 232 will be located upstream of the flapper 231, and a downstream pressure port 234 will be located downstream of the flapper 231. By such arrangement, pressures may be concurrently measured through upstream pressure port 232 and downstream pressure port 234 to determine the difference in pressures upstream and downstream of the flapper 231.

As expiratory gas flow passes outwardly, through the outlet port of the exhalation valve 18, the flapper portion 231 of the flow transducer 230 will deflect or move allowing such expiratory gas flow to pass thereacross, but also creating a moderate flow restriction. The flow restriction created by the flow transducer 230 results in a pressure differential being developed across the flow transducer 230. Such pressure differential may be monitored by pressure ports 232 and 234 disposed on opposite side of the flow transducer 230 (as shown in FIG. 11a) which pressure ports are in flow communication by internal passages formed within the housing segment 200c, 200b and 200a to tubing connections 240 and 235. A manifold insert 201 may be mounted on the upstream pressure port 232 such that the manifold insert 201 protrudes into the expiratory flowpath 206, upstream of the flapper 231. A plurality of inlet apertures 201a, preferably four in number are formed around the outer sidewall of the manifold insert 201, and communicate through a common central passageway with the upstream pressure port 232, thereby facilitating accurate measurement of the pressure within the expiratory flowpath 206 at that location.

An exhalation differential pressure transducer 70 (shown in FIG. 2) may be located within the housing or enclosure of the ventilator 10. The exhalation differential pressure transducer 70 is connected by way of tubing to the first and third pressure port tubing connectors 240 and 235 so as to continuously measure and provide the controller 12 with the difference between pressure upstream (P1) and pressure downstream (P2) of the flow transducer 230. The difference in pressure determined by the exhalation differential pressure transducer 70 is communicated to the controller, and the controller is operatively programmed to calculate the actual flow rate at which expiratory gas is exiting the flow channel 206. As will be recognized, the exhalation flow rate may be utilized by the controller 12 for differing purposes such as triggering of initiation of the next inspiratory cycle.

Although the particular formation and mounting structure utilized for the exhalation flow transducer 230 provides exceptional accuracy in most situations, the applicant has found that in certain circumstances, it is desirable to eliminate any inaccuracies caused by manufacturing and assembly tolerances. As such, in the preferred embodiment, the specific operational characteristics of each exhalation flow transducer 230, i.e., pressure differential for specific flow rates are measured for calibration purposes and stored on a storage medium contained within the exhalation valve housing 18. In the preferred embodiment this specific characterization and calibration information is encoded on a radio frequency transponder 203 of the type commercially available under the product name Tiris, manufactured by Texas Instruments, of Austin, Tex. The radio-frequency transponder 203 and its associated transmitter/receiver antenna 203a may be mounted within the exhalation valve housing 200 as shown in FIG. 11c. Additionally, a radio frequency transmitter/receiver is positioned within the ventilator system 10, such that upon command of the controller 12, the calibration and characterization data contained within the transponder 203 is transmitted via radio frequency to the receiver and stored within the controller 12. Subsequently, the controller 12 utilizes such stored calibration and characterization data to specifically determine expiratory flow rate based upon pressure differential values generated by the differential pressure transducer 70.

F. A Preferred Auto Calibration Circuit

In the preferred embodiment, the ventilator device 14 of the ventilator system 10 of the present invention incorporates an auto calibration circuit for periodic rezeroing of the system to avoid errors in the tidal volume or inspiratory flow delivered by the drag compressor 30.

In particular, as shown in FIG. 2 the preferred auto calibration circuit comprises the following components:

a) a first auto-zero valve 74 on the line between the inlet 32 of the compressor 30 and the differential pressure transducer 36;

b) a second auto-zero valve 76 on the line between the first pressure port of the exhalation valve 18 and the first pressure (P1) side of the exhalation differential pressure transducer 70;

c) a third auto-zero valve 80 on the line between the second pressure (P2) port 234 of the exhalation valve 18 and the second pressure (P2) side of the exhalation differential pressure transducer 70;

d) a fourth auto-zero valve 78 on the line between the outlet port 34 and the differential pressure transducer 36; and e) and a fifth auto-zero valve 72 on the line between the airway pressure port 241 and the airway pressure transducer 68.

Each of the auto-zero valves 72, 74, 76, 78, 80 is connected to the controller 12 such that, at selected time intervals during the ventilatory cycle, the controller 12 may signal the auto-zero valves 72, 74, 76, 78, 80 to open to atmospheric pressure. While the auto-zero valve 72, 74, 76, 78, 80 are open to atmospheric pressure, the controller 12 may re-zero each of the transducers 36, 68, 70 to which the respective auto-zero valve 72, 74, 76, 80 are connected. Such periodic re-zeroing of the pressure transducers 36, 68 and 70 will correct any baseline (zero) drift which has occurred during operation.

Ventilator Operation

With the structure defined, the basic operation of the ventilator system 10 of the present invention may be described. As will be recognized, the particular ventilatory mode selected by a technician may be input to the controller 12 via the input controls upon the display 380. Additionally, the technician must attach the inspiratory and exhalation tubing circuit to the patient PT as illustrated in FIG. 1.

Prior to initiation of patient ventilation, the controller 12 initiates its auto calibration circuit and system check to insure that all system parameters are within operational specifications. Subsequently, inspiration is initiated wherein the controller 12 rapidly accelerates the drag compressor 30. During such acceleration, air is drawn through the filter 50, accumulator 54 and supplied to the patient PT, via line 22. During such inspiratory phase, the controller 12 monitors the pressure drop across the compressor 30, via pressure transducer 36, and the rotational speed of the rotor 104. This data is then converted to flow by the controller 12 via the turbine characterization table to insure that the proper flow and volume of inspiratory gas is delivered to the patient PT. Additionally, during such inspiratory phase, the exhalation valve 18 is maintained in a closed position. In those applications where oxygen blending is desired, the controller 12 additionally opens selected ones of the solenoid valve 52a, 52b, 52c, 52d and 52e, in timed sequence to deliver a desired volume of oxygen to the accumulator 54, which is subsequently delivered to the patient PT during inspiratory flow conditions.

When inspiratory flow is desired to be terminated, the controller 12 rapidly stops or decelerates the drag compressor 30 to a basal rotational speed, and the patient is free to exhale through exhalation line 66 and through the exhalation valve 18. Depending upon desired ventilation mode operation, the controller 12 monitors the exhalation pressure, via pressure transducer 68 connected to the airway passage and adjusts the position of the valve relative the valve seat within the exhalation valve 18 to maintain desired airway pressures. Simultaneously, the controller 12 monitors the pressure differential existing across the exhalation flow transducer 230 via exhalation pressure transducer 70 to compute exhaled flow. This exhaled flow is used to compute exhaled volume and to determine a patient trigger. When a breath is called for either through a machine or patient trigger, the controller initiates a subsequent inspiratory flow cycle with subsequent operation of the ventilator system 10 being repeated between inspiratory and exhalation cycles.

Those skilled in the art will recognize that differing ventilation modes, such as intermittent mandatory ventilation (IMV), synchronized intermittent mandatory ventilation (SMIV) controlled mechanical ventilation (CMV) and assist control ventilation (A/C), are all available modes of operation on the ventilator 10 of the present invention. Further those skilled in the art will recognize that by proper selection of control inputs to the ventilator 10, all modern breath types utilized in clinical practice, may be selected, such as machine cycled mandatory breath, machine cycled assist breath, patient cycled supported breath, patient cycled spontaneous breath, volume controlled mandatory breaths, volume controlled assist breaths, pressure controlled breaths, pressure support breaths, sigh breaths, proportional assist ventilation and volume assured pressure support.

What is claimed is:

1. A portable compressor ventilator device for ventilating the lungs of a mammalian patient, said device comprising:
    a compressor and an oxygen blending apparatus for combining oxygen with ambient air into an oxygen-enriched inspiratory flow containing a prescribed oxygen concentration prior to entering the compressor;
    a tubing circuit in air communication with the oxygen blending apparatus wherein the tubing circuit is sized and configured to interface with the mammalian patient for delivering the combined oxygen/ambient air directly to the mammalian patient;
    a controller that controls the compressor and the oxygen blending apparatus; and
    a battery that supplies power to the blending apparatus and the controller;
    wherein the oxygen blending apparatus comprises:
    an oxygen inflow manifold;
    an oxygen outflow manifold;
    an accumulator connected to the oxygen outflow manifold and an input of the compressor;
    a plurality of solenoid valves arranged in parallel between the oxygen inflow manifold and the oxygen outflow manifold;
    wherein each of the solenoid valves has a specific sized flow restricting orifice, a first solenoid valve of the plurality of solenoid valves having a different sized flow restricting orifice compared to a second solenoid valve of the plurality of solenoid valves; and
    wherein each of the solenoid valves has a predetermined trigger volume, the controller independently opening each of the solenoid valves when an accumulated volume of the combined oxygen/ambient air drawn from the accumulator reaches the trigger volume.

2. The ventilator device of claim 1, further comprising an air conduit conveying the ambient air to the accumulator.

3. The ventilator device of claim 1, wherein the controller opens and closes the individual solenoid valves for predetermined periods of time, so as to provide a metered flow of oxygen through the oxygen outflow manifold and into the accumulator.

4. The ventilator device of claim 1, further comprising a filter for filtering the ambient air before entering the accumulator.

5. The ventilator device of claim 1 wherein the compressor is a rotary compressor.

6. The ventilator device of claim 1 wherein the tubing circuit comprises an inspiratory tube for delivering the combined oxygen/ambient air to the patient and an exhalation tube for removing breathed air from the mammalian patient.

7. A portable compressor ventilator device for ventilating the lungs of a mammalian patient, said device comprising:
    an oxygen blending apparatus for combining oxygen with ambient air, the oxygen blending apparatus comprising:
    an oxygen inflow manifold;
    an oxygen outflow manifold;
    a plurality of solenoid valves in parallel with each other and disposed between the oxygen inflow manifold and the oxygen outflow manifold;
    a controller in communication with the plurality of solenoid valves and operative to actuate selective combination of the solenoid valves to adjust an aggregate flow rate of the combined oxygen/ambient air through the oxygen outflow manifold; and
    a battery that supplies power to the blending apparatus and the controller,
    wherein a first solenoid valve of the plurality of solenoid valves has a different sized flow restricting orifice compared to a second solenoid valve of the plurality of solenoid valves; and
    wherein each of the solenoid valves has a predetermined trigger volume, the controller independently opening each of the solenoid valves when a volume of the combined oxygen/ambient air drawn through the compressor reaches the trigger volume.

8. The device of claim 7 wherein the controller is operative to open at least two of the solenoid valves simultaneously to adjust the aggregate flow rate of the combined oxygen/ambient air through the oxygen outflow manifold.

9. The device of claim 7 wherein the controller is operative to open a combination of the solenoid valves to adjust an aggregate flow rate of the combined oxygen/ambient air through the oxygen outflow manifold.

* * * * *